(12) United States Patent
Ducray et al.

(10) Patent No.: US 7,091,371 B2
(45) Date of Patent: Aug. 15, 2006

(54) AMINOACETONITRILE DERIVATIVES AND THEIR USE FOR CONTROLLING PARASITES

(75) Inventors: Pierre Ducray, Saint-Louis (FR); Thomas Goebel, Lorrach (DE)

(73) Assignee: Novartis Animal Health US, Inc., Greensboro, NC (US)

( * ) Notice: Subject to any disclaimer, the term of this patent is extended or adjusted under 35 U.S.C. 154(b) by 134 days.

(21) Appl. No.: 10/496,620

(22) PCT Filed: Dec. 5, 2002

(86) PCT No.: PCT/EP02/13811

§ 371 (c)(1),
(2), (4) Date: May 25, 2004

(87) PCT Pub. No.: WO03/048112

PCT Pub. Date: Jun. 12, 2003

(65) Prior Publication Data

US 2005/0033081 A1  Feb. 10, 2005

(30) Foreign Application Priority Data

Dec. 6, 2001 (CH) .................................. 2225/01

(51) Int. Cl.
*C07C 255/44* (2006.01)
(52) U.S. Cl. ..................................... 558/392

(58) Field of Classification Search ................. 558/392
See application file for complete search history.

(56) References Cited

U.S. PATENT DOCUMENTS 3,457,294 A * 7/1969 Neundorf et al. ........... 558/392

FOREIGN PATENT DOCUMENTS

| EP | 0 943 565 | 11/1999 |
| WO | WO 02 49641 | 6/2002 |

* cited by examiner

*Primary Examiner*—Johann Richter
*Assistant Examiner*—Ebenezer Sackey
(74) *Attorney, Agent, or Firm*—David L. Marks

(57) ABSTRACT

The invention relates to compounds of the general formula (I), in which $R_1$, $R_2$, X, $Ar_1$ and $Ar_2$ are as defined in claim 1, and to any enantiomers thereof. The active ingredients have advantageous pesticidal properties. They are particularly suitable for controlling parasites in warm-blooded animals

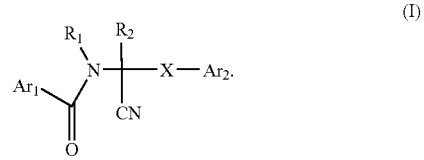

(I)

28 Claims, No Drawings

AMINOACETONITRILE DERIVATIVES AND THEIR USE FOR CONTROLLING PARASITES

This application is a National Phase Application under § 371 of International Application Number PCT/EP02/13811 filed on Dec. 5, 2002.

The present invention relates to novel amidoacetonitrile compounds of the formula

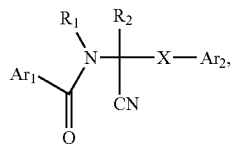

in which $Ar_1$ and $Ar_2$ are, independently of one another, unsubstituted or mono- or polysubstituted phenyl, in which the substituents can be independent of one another and are chosen from the group consisting of halogen, nitro, cyano, $C_1-C_6$alkyl, halo-$C_1-C_6$alkyl, $C_1-C_6$alkoxy, halo-$C_1-C_6$alkoxy, $C_2-C_6$alkenyl, halo-$C_2-C_6$alkenyl, 02-$C_6$alkynyl, $C_3-C_6$cycloalkyl, $C_3-C_6$cycloalkyl-oxy, $C_3-C_6$cycloalkylamino, $C_3-C_6$cycloalkylthio, $C_2-C_6$alkenyloxy, halo-$C_2-C_6$alkenyloxy, $C_1-C_6$alkylthio, halo-$C_1-C_6$alkylthio, $C_1-C_6$alkylsulfonyloxy, halo-$C_1-C_6$alkylsulfonyloxy, $C_1-C_6$alkylsulfinyl, halo-$C_1-C_6$alkylsulfinyl, $C_1-C_6$alkylsulfonyl, halo-$C_1-C_6$alkylsulfonyl, $C_2-C_6$alkenylthio, halo-$C_2-C_6$alkenylthio, $C_2-C_6$alkenylsulfinyl, halo-$C_2-C_6$alkenylsulfinyl, $C_2-C_6$alkenylsulfonyl, halo-$C_2-C_6$alkenylsulfonyl, $C_1-C_6$alkylamino, di-$C_1-C_6$alkylamino, $C_1-C_6$alkylsulfonylamino, halo-$C_1-C_6$alkylsulfonylamino, $C_1-C_6$alkylcarbonyl, halo-$C_1-C_6$alkylcarbonyl, $C_1-C_6$alkoxycarbonyl, $C_1-C_6$alkylaminocarbonyl and di-$C_1-C_6$alkylaminocarbonyl; unsubstituted or mono- or polysubstituted phenylamino; unsubstituted or mono- or polysubstituted phenylcarbonyl; unsubstituted or mono- or poly-substituted phenylmethoxyimino; unsubstituted or mono- or polysubstituted phenylhydroxy-methyl; unsubstituted or mono- or polysubstituted 1-phenyl-1-hydroxyethyl; unsubstituted or mono- or polysubstituted phenylchloromethyl; unsubstituted or mono- or polysubstituted phenylcyanomethyl; unsubstituted or mono- or polysubstituted phenyl, in which the substituents in each case can be independent of one another and are chosen from the group consisting of halogen, nitro, cyano, $C_1-C_6$alkyl, halo-$C_1-C_6$alkyl, $C_1-C_6$alkoxy, halo-$C_1-C_6$alkoxy, $C_1-C_6$alkylthio, halo-$C_1-C_6$alkylthio, $C_1-C_6$alkylsulfinyl, halo-$C_1-C_6$alkylsulfinyl, $C_1-C_6$alkylsulfonyl and halo-$C_1-C_6$alkylsulfonyl; unsubstituted or mono- or polysubstituted phenoxy, in which the substituents can be independent of one another and are chosen from the group consisting of halogen, nitro, cyano, $C_1-C_6$alkyl, halo-$C_1-C_6$alkyl, $C_1-C_6$alkoxy, halo-$C_1-C_6$alkoxy, $C_1-C_6$alkylthio, halo-$C_1-C_6$alkylthio, $C_1-C_6$alkylsulfinyl, halo-$C_1-C_6$alkylsulfinyl, $C_1-C_6$alkylsulfonyl and halo-$C_1-C_6$alkylsulfonyl; unsubstituted or mono- or polysubstituted phenylacetylenyl, in which the substituents can be independent of one another and are chosen from the group consisting of halogen, nitro, cyano, $C_1-C_6$alkyl, halo-$C_1-C_6$alkyl, $C_1-C_6$alkoxy, halo-$C_1-C_6$alkoxy, $C_1-C_6$alkylthio, halo-$C_1-C_6$alkylthio, $C_1-C_6$alkylsulfinyl, halo-$C_1-C_6$alkylsulfinyl, $C_1-C_6$alkylsulfonyl and halo-$C_1-C_6$alkylsulfonyl; and unsubstituted or mono- or polysubstituted pyridyloxy, in which the substituents can be independent of one another and are chosen from the group consisting of halogen, nitro, cyano, $C_1-C_6$alkyl, halo-$C_1-C_6$alkyl, $C_1-C_6$alkoxy, halo-$C_1-C_6$alkoxy, $C_1-C_6$alkylthio, halo-$C_1-C_6$alkylthio, $C_1-C_6$alkylsulfinyl, halo-$C_1-C_6$alkylsulfinyl, $C_1-C_6$alkylsulfonyl and halo-$C_1-C_6$alkylsulfonyl;

unsubstituted or mono- or polysubstituted hetaryl, in which the substituents can be independent of one another and are chosen from the group consisting of halogen, nitro, cyano, $C_1-C_6$alkyl, halo-$C_1-C_6$alkyl, $C_1-C_6$alkoxy, halo-$C_1-C_6$alkoxy, $C_2-C_6$alkenyloxy, halo-$C_2-C_6$alkenyloxy, $C_1-C_6$alkylthio, halo-$C_1-C_6$alkylthio, $C_1-C_6$alkylsulfinyl, halo-$C_1-C_6$alkylsulfinyl, $C_2-C_6$alkenylthio, halo-$C_2-C_6$alkenylthio, $C_2-C_6$alkenylsulfinyl, halo-$C_2-C_6$alkenylsulfinyl, $C_1-C_6$alkylsulfonyl, halo-$C_1-C_6$alkylsulfonyl, $C_2-C_6$alkenylsulfonyl, halo-$C_2-C_6$alkenylsulfonyl, $C_1-C_6$alkylamino and di-$C_1-C_6$alkylamino; or unsubstituted or mono- or polysubstituted naphthyl or quinolyl, in which the substituents can be independent of one another and are chosen from the group consisting of halogen, nitro, cyano, $C_1-C_6$alkyl, halo-$C_1-C_6$alkyl, $C_1-C_6$alkoxy, halo-$C_1-C_6$alkoxy, $C_2-C_6$alkenyloxy, halo-$C_2-C_6$alkenyloxy, $C_1-C_6$alkylthio, halo-$C_1-C_6$alkylthio, $C_1-C_6$alkylsulfinyl, halo-$C_1-C_6$alkylsulfinyl, $C_2-C_6$alkenylthio, halo-$C_2-C_6$alkenylthio, $C_2-C_6$alkenylsulfinyl, halo-$C_2-C_6$alkenylsulfinyl, $C_1-C_6$alkylsulfonyl, halo-$C_1-C_6$alkylsulfonyl, $C_2-C_6$alkenylsulfonyl, halo-$C_2-C_6$alkenylsulfonyl, $C_1-C_6$alkylamino and di-$C_1-C_6$alkylamino;

$R_1$ is hydrogen, $C_1-C_6$alkyl, halo-$C_1-C_6$alkyl, allyl or $C_1-C_6$alkoxymethyl;

$R_2$, $R_3$, $R_4$, $R_5$, $R_6$, $R_7$ and $R_8$ are either, independently of one another, hydrogen, halogen, unsubstituted or mono- or polyhalogenated $C_1-C_6$alkyl, unsubstituted or mono- or polyhalogenated $C_2-C_6$alkenyl, unsubstituted or mono- or polyhalogenated $C_2-C_6$alkynyl; unsubstituted or mono- or polysubstituted $C_1-C_6$alkoxy, unsubstituted or mono- or polysubstituted halo-$C_1-C_6$alkoxy, unsubstituted or mono- or polysubstituted $C_3-C_6$cycloalkyl, in which the substituents in each case can be independent of one another and are chosen from the group consisting of halogen and $C_1-C_6$alkyl; or unsubstituted or mono- or polysubstituted phenyl, in which the substituents can be independent of one another and are chosen from the group consisting of halogen, nitro, cyano, $C_1-C_6$alkyl, halo-$C_1-C_6$alkyl, $C_1-C_6$alkoxy, halo-$C_1-C_6$alkoxy, $C_1-C_6$alkylthio, halo-$C_1-C_6$alkylthio, $C_1-C_6$alkylsulfinyl, halo-$C_1-C_6$alkylsulfinyl, $C_1-C_6$alkylsulfonyl, halo-$C_1-C_6$alkylsulfonyl, $C_0-C_6$alkylamino or di-$C_1-C_6$alkylamino;

or $R_2$ and $R_3$ are jointly $C_2-C_6$alkylene; and

X is $C(R_3)(R_4)-C(R_5)(R_6)$ or $C(R_7)=C(R_8)$;

to their preparation and use in the control of endo- and ectoparasites, especially helminths, in and on warm-blooded productive livestock, domestic animals and plants, and also to pesticides which comprise at least one of these compounds.

Substituted amidoacetonitrile compounds with pesticidal action are disclosed in EP-O 953 565 A2, for example. The active ingredients specifically revealed therein may not, however, always meet the requirements concerning strength and activity spectrum. There consequently exists a need for active ingredients with improved pesticidal properties. It has now been found that the amidoacetonitrile compounds of the formula I have outstanding pesticidal properties, in particular against endo- and ectoparasites in and on productive livestock, domestic animals and plants.

Alkyl—as group per se and as structural component of other groups and compounds, for example of haloalkyl, alkoxy, alkylthio, alkylsulfinyl and alkylsulfonyl,—is, in each case giving due consideration to the number of carbon atoms which the relevant group or compound has in each individual case, either straight-chain, i.e. methyl, ethyl, propyl, butyl, pentyl or hexyl, or branched, e.g. isopropyl, isobutyl, sec-butyl, tert-butyl, isopentyl, neopentyl or isohexyl.

Alkenyl —as group per se and as structural component of other groups and compounds —is, in each case giving due consideration to the number of carbon atoms and conjugated or isolated double bonds which the relevant group or compound has in each individual case, either straight-chain, e.g. allyl, 2-butenyl, 3-pentenyl, 1-hexenyl or 1,3-hexadienyl, or branched, e.g. isopropenyl, isobutenyl, Isoprenyl, tert-pentenyl or isohexenyl.

Alkynyl —as group per se and as structural component of other groups and compounds —is, in each case giving due consideration to the number of carbon atoms and conjugated or isolated double bonds which the relevant group or compound has in each individual case, either straight-chain, e.g. propargyl, 2-butynyl, 3-pentynyl, 1-hexynyl, 1-heptynyl or 3-hexen-1-ynyl, or branched, e.g. 3-methylbut-1-ynyl, 4-ethylpent-1-ynyl or 4-methylhex-2-ynyl.

Cycloalkyl —as group per se and as structural component of other groups and compounds, for example of halocycloalkyl, cycloalkoxy or cycloalkylthio, —is, in each case giving due consideration to the number of carbon atoms which the relevant group or compound has in each individual case, cyclopropyl, cyclobutyl, cyclopentyl or cyclohexyl.

Hetaryl is pyridyl, pyrimidyl, s-triazinyl, 1,2,4-triazinyl, thienyl, furanyl, pyrroyl, pyrazolyl, imidazolyl, thiazolyl, triazolyl, oxazolyl, thiadiazolyl, oxadiazolyl, benzothienyl, benzofuranyl, benzothiazolyl, indolyl or indazolyl, preferably pyridyl, pyrimidyl, s-triazinyl or 1,2,4-triazinyl, in particular pyridyl or pyrimidyl.

Halogen —as group per se and as structural component of other groups and compounds, such as of haloalkyl, haloalkoxy, haloalkylthio, haloalkylsulfinyl and haloalkylsulfonyl, —is fluorine, chlorine, bromine or iodine, in particular fluorine, chlorine or bromine, especially fluorine or chlorine.

Halogen-substituted carbon-comprising groups and compounds, such as haloalkyl, halo-alkoxy, haloalkylthio, haloalkylsulfinyl and haloalkylsulfonyl, can be partially halogenated or perhalogenated, it being possible, in the case of polyhalogenation, for the halogen substituents to be identical or different. Examples of haloalkyl —as group per se and as structural component of other groups and compounds, such as of haloalkoxy or haloalkylthio, —are methyl substituted up to three times by fluorine, chlorine and/or bromine, such as $CHF_2$ or $CF_3$; ethyl substituted up to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted up to seven times by fluorine, chlorine and/or bromine, such as $CH_2CHBrCH_2Br$, $CF_2CHFCF_3$, $CH_2CF_2CF_3$ or $CH(CF_3)_2$; butyl or one of its isomers substituted up to nine times by fluorine, chlorine and/or bromine, such as $CF(CF_3)CHFCF_3$ or $CH_2(CF_2)_2CF_3$; pentyl or one of its isomers substituted up to eleven times by fluorine, chlorine and/or bromine, such as $CF(CF_3)(CHF)_2CF_3$ or $CH_2(CF_2)_3CF_3$; and hexyl or one of its isomers substituted up to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Alkoxy groups preferably have a chain length of 1 to 6 carbon atoms. For example, alkoxy is methoxy, ethoxy, propoxy, isopropoxy, n-butoxy, isobutoxy, sec-butoxy and tert-butoxy, and also the pentyloxy and hexyloxy isomers; preferably methoxy and ethoxy. Haloalkoxy groups preferably have a chain length of 1 to 6 carbon atoms. Haloalkoxy is, e.g., fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Preferred embodiments within the context of the invention are:

(1) a compound of the formula I, in which Arm and $Ar_2$ are, independently of one another, unsubstituted or mono- or polysubstituted phenyl, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_3$–$C_5$cycloalkyl, $C_3$–$C_5$cycloalkyloxy, $C_3$–$C_5$cycloalkylamino, $C_1$–$C_5$alkylthio, halo-$C_1$–$C_5$alkylthio, $C_1$–$C_4$alkylamino, di-$C_1$–$C_4$alkylamino, $C_1$–$C_4$alkylcarbonyl, halo-$C_1$–$C_4$alkylcarbonyl, $C_1$–$C_4$alkoxycarbonyl, $C_1$–$C_4$alkylaminocarbonyl and di-$C_1$–$C_4$alkylaminocarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio; unsubstituted or mono- or polysubstituted phenoxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio; and unsubstituted or mono- or polysubstituted pyridyloxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio;

particularly, independently of one another, unsubstituted or mono- or polysubstituted phenyl, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_3$–$C_5$cycloalkyl, $C_3$–$C_5$cycloalkyloxy, $C_3$–$C_5$cycloalkylamino, $C_1$–$C_4$alkylcarbonyl, halo-$C_1$–$C_4$alkylcarbonyl and $C_1$–$C_4$alkoxycarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, nitro, cyano, $C_1$–$C_4$alkyl, halo-$C_1$–$C_4$alkyl, $C_1$–$C_4$alkoxy and halo-$C_1$–$C_4$alkoxy; and unsubstituted or mono- or polysubstituted phenoxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy and halo-$C_1$–$C_4$alkoxy;

very particularly, independently of one another, unsubstituted or mono- or polysubstituted phenyl, in which the substituents can be independent of one another and are chosen from the group consisting of halogen, cyano, $C_1$–$C_2$alkyl, halo-$C_1$–$C_2$alkyl, $C_1$–$C_2$alkoxy, halo-$C_0$–$C_2$alkoxy, $C_3$–$C_4$cycloalkyl, $C_3$–$C_4$cycloalkyloxy, $C_3$–$C_4$cycloalkylamino, $C_1$–$C_2$alkylcarbonyl, halo-$C_1$–$C_2$alkylcarbonyl and $C_1$–$C_2$alkoxycarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, cyano, $C_1$–$C_2$alkyl, halo-$C_1$–$C_2$alkyl, $C_1$–$C_2$alkoxy and halo-$C_1$–$C_2$alkoxy; and unsubstituted or mono- or polysubstituted phenoxy, in which the substituents can be independent of one another and are chosen from the group consisting of halogen, cyano, $C_1$–$C_2$alkyl, halo-$C_1$–$C_2$alkyl, $C_1$–$C_2$alkoxy and halo-$C_1$–$C_2$alkoxy;

(2) a compound of the formula I, in which $R_1$ is hydrogen, $C_1$–$C_4$alkyl or halo-$C_1$–$C_4$alkyl;

particularly hydrogen or $C_1$–$C_2$alkyl;

very particularly hydrogen;

(3) a compound of the formula I, in which $R_2$, $R_3$, $R_4$, $R_5$, $R_6$, $R_7$ and $R_8$ are, independently of one another, hydrogen, halogen, unsubstituted or mono- or polyhalogenated $C_1$–$C_4$alkyl, unsubstituted or mono- or polyhalogenated $C_2$–$C_4$alkenyl, unsubstituted or mono- or polyhalogenated $C_2$–$C_4$alkynyl; unsubstituted or mono- or polysubstituted $C_1$–$C_4$alkoxy, unsubstituted or mono- or polysubstituted halo-$C_1$–$C_4$alkoxy, $C_3$–$C_5$cycloalkyl, or unsubstituted or mono- or polysubstituted phenyl, in which the substituents can be independent of one another and are chosen from the group consisting of halogen, cyano, $C_1$–$C_4$alkyl, halo-$C_1$–$C_4$alkyl, $C_1$–$C_4$alkoxy and halo-$C_1$–$C_4$alkoxy;

particularly, independently of one another, hydrogen, unsubstituted or mono- or polyhalogenated $C_1$–$C_4$alkyl, $C_3$–$C_5$cycloalkyl, or unsubstituted or mono- or polysubstituted phenyl, in which the substituents can be independent of one another and are chosen from the group consisting of halogen, $C_1$–$C_2$alkyl or halo-$C_1$–$C_4$alkyl;

very particularly, independently of one another, hydrogen, $C_1$–$C_2$alkyl or $C_3$–$C_5$cycloalkyl;

(4) a compound of the formula I, in which X is $C(R_3)(R_4)$—$C(R_5)(R_6)$;

(5) a compound of the formula I, in which Ar and $Ar_2$ are, independently of one another, unsubstituted or mono- or polysubstituted phenyl, in which the substituents can be independent of one another and are chosen from the group consisting of halogen, nitro, cyano, $C_1$–$C_4$alkyl, halo-$C_1$–$C_4$-alkyl, $C_1$–$C_4$alkoxy, halo-$C_1$–$C_4$alkoxy, $C_3$–$C_5$cycloalkyl, $C_3$–$C_5$cycloalkyloxy, $C_3$–$C_5$cycloalkylamino, $C_1$–$C_5$alkylthio, halo-$C_1$–$C_5$alkylthio, $C_1$–$C_4$alkylamino, di-$C_1$–$C_4$alkylamino, $C_1$–$C_4$alkylcarbonyl, halo-$C_1$–$C_4$alkylcarbonyl, $C_1$–$C_4$alkoxycarbonyl, $C_1$–$C_4$alkylaminocarbonyl and di-$C_1$–$C_4$alkylaminocarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio; unsubstituted or mono- or polysubstituted phenoxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio; and unsubstituted or mono- or polysubstituted pyridyloxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio;

$R_1$ is hydrogen, $C_1$–$C_4$alkyl or halo-$C_1$–$C_4$alkyl;

$R_2$, $R_3$, $R_4$, $R_5$, $R_5$, $R_7$ and $R_6$ are, independently of one another, hydrogen, halogen, unsubstituted or mono- or polyhalogenated $C_1$–$C_4$alkyl, unsubstituted or mono- or polyhalogenated $C_2$–$C_4$alkenyl, unsubstituted or mono- or polyhalogenated $C_2$–$C_4$alkynyl; unsubstituted or mono- or polysubstituted $C_1$–$C_4$alkoxy, unsubstituted or mono- or polysubstituted halo-$C_1$–$C_4$alkoxy, $C_3$–$C_5$cycloalkyl, or unsubstituted or mono- or polysubstituted phenyl, in which the substituents can be independent of one another and are chosen from the group consisting of halogen, cyano, $C_1$–$C_4$alkyl, halo-$C_1$–$C_4$alkyl, $C_1$–$C_4$alkoxy and halo-$C_1$–$C_4$alkoxy; and X is $C(R_3)(R_4)$—$C(R_5)(R_6)$;

(6) a compound of the formula I, in which $Ar_1$ and $Ar_2$ are particularly, independently of one another, unsubstituted or mono- or polysubstituted phenyl, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_3$–$C_5$cycloalkyl, $C_3$–$C_5$cycloalkyloxy, $C_3$–$C_6$cycloalkylamino, $C_1$–$C_4$alkylcarbonyl, halo-$C_1$–$C_4$alkylcarbonyl and $C_1$–$C_4$alkoxycarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, nitro, cyano, $C_1$–$C_4$alkyl, halo-$C_1$–$C_4$alkyl, $C_1$–$C_4$alkoxy and halo-$C_1$–$C_4$alkoxy; and unsubstituted or mono- or polysubstituted phenoxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy and halo-$C_1$–$C_4$alkoxy;

$R_1$ is hydrogen or $C_1$–$C_2$alkyl;

$R_2$, $R_3$, $R_4$, $R_5$, $R_6$, $R_7$ and $R_8$ are, independently of one another, hydrogen, unsubstituted or mono- or polyhalogenated $C_1$–$C_4$alkyl, $C_3$–$C_5$cycloalkyl, or unsubstituted or mono- or polysubstituted phenyl, in which the substituents can be independent of one another and are chosen from the group consisting of halogen, $C_1$–$C_2$alkyl or halo-$C_1$–$C_4$alkyl; and X is $C(R_3)(R_4)$—$C(R_5)(R_6)$;

(7) a compound of the formula I, in which $Ar_1$ and $Ar_2$ are, independently of one another, unsubstituted or mono- or polysubstituted phenyl, in which the substituents can be independent of one another and are chosen from the group consisting of halogen, cyano, $C_1$–$C_2$alkyl, halo-$C_1$–$C_2$alkyl, $C_1$–$C_2$alkoxy, halo-$C_1$–$C_2$alkoxy, $C_3$–$C_4$cycloalkyl, $C_3$–$C_4$cyclo-alkyloxy, $C_3$–$C_4$cycloalkylamino, $C_1$–$C_2$alkylcarbonyl, halo-$C_1$–$C_2$alkylcarbonyl and $C_1$–$C_2$alkoxycarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, cyano, $C_1$–$C_2$alkyl, halo-$C_1$–$C_2$alkyl, $C_1$–$C_2$alkoxy and halo-$C_1$–$C_2$alkoxy; and unsubstituted or mono- or polysubstituted phenoxy, in which the substituents can be independent of one another and are chosen from the group consisting of halogen, cyano, $C_1$–$C_2$alkyl, halo-$C_1$–$C_2$alkyl, $C_1$–$C_2$alkoxy and halo-$C_1$–$C_2$alkoxy;

$R_1$ is hydrogen;

$R_2$, $R_3$, $R_4$, $R_5$, $R_6$, $R_7$ and $R_8$ are, independently of one another, hydrogen, $C_1$–$C_2$alkyl or $C_3$–$C_5$cycloalkyl; and X is $C(R_3)(R_4)$—$C(R_5)(R_6)$.

The compounds of the formula I listed in Table 1 are particularly preferred within the context of the invention and the compounds of the formula I mentioned in the synthetic examples are very particularly preferred.

A further subject-matter of the invention is the process for the preparation of the compounds of the formula I, in each case in the free form or in the salt form, e.g. which comprises the reaction of a compound of the formula

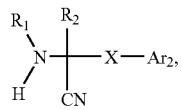

II which is known or can be prepared by analogy to relevant known compounds and in which $R_1$, $R_2$, X and $Ar_2$ are as defined above in the formula I, with a compound of the formula

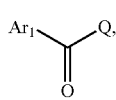

III which is known or can be prepared by analogy to relevant known compounds and in which $Ar_1$ is as defined above in the formula I and Q is a leaving group, if desired in the presence of a basic catalyst, and in each case, if desired, the conversion of a compound of the formula I obtainable according to the process or in another way, in each case in the free form or in the salt form, to another compound of the formula I, the separation of a mixture of isomers obtainable according to the process and the isolation of the desired isomer and/or the conversion of a free compound of the formula I obtainable according to the process to the salt or the conversion of a salt of a compound of the formula I obtainable according to the process to the free compound of the formula I or to another salt.

That which has been said above for salts of compounds I applies analogously to starting materials mentioned hereinabove and hereinafter with regard to the salts thereof.

The reactants can be reacted with one another as such, i.e. without addition of a solvent or diluent, e.g. in the molten form. For the most part, however, it is advantageous to add an inert solvent or diluent or a mixture thereof. Mention may be made, as examples of such solvents or diluents, of: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethyl-formamide, N,N-diethylformamide, N,N-dimethylacetamide, N-methylpyrrolidone or hexamethylphosphoramide; nitriles, such as acetonitrile or propionitrile; and sulfoxides, such as dimethyl sulfoxide.

Preferred leaving groups Q are halogens, tosylates, mesylates and triflates, particularly preferably halogens, especially chlorine.

Suitable bases for facilitating the reaction are, e.g., alkali metal or alkaline earth metal hydroxides, hydrides, amides, alkoxides, acetates, carbonates, dialkylamides or alkyl-silylamides, alkylamines, alkylenediamines, if desired N-alkylated and saturated or unsaturated, cycloalkylamines, basic heterocycles, ammonium hydroxides and carbocyclic amines. Mention may be made, by way of examples, of sodium hydroxide, sodium hydride, sodamide, sodium methoxide, sodium acetate, sodium carbonate, potassium t-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU). Diisopropylethylamine and 4-(N,N-dimethylamino)pyridine are preferred.

The reaction is advantageously carried out at a temperature from approximately 0° C. to approximately +10° C., preferably from approximately 10° C. to approximately +40° C.

In a preferred process, a compound of the formula II is reacted at ambient temperature in a halogenated hydrocarbon, preferably dichloromethane, with a compound of the formula III in the presence of a base, preferably a mixture of diisopropylethylamine and 4-(N,N-dimethylamino)pyridine.

A further subject-matter of the invention is the process for the preparation of the compounds of the formula II, in each case in the free form or in the salt form, e.g. which comprises the reaction of a compound of the formula

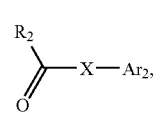

IV which is known or can be prepared by analogy to relevant known compounds and in which $R_2$, X and $Ar_2$ are as defined in formula I, with an inorganic or organic cyanide and a compound of the formula $R_1$—$NH_2$, which is known or can be prepared by analogy to relevant known compounds and in which $R_1$ is as defined in the formula I, and in each case, if desired, the conversion of a compound of the formula II obtainable according to the process or in another way, in each case in the free form or in the salt form, to another compound of the formula II, the separation of a mixture of isomers obtainable according to the process and the isolation of the desired isomer and/or the conversion of a free compound of the formula II obtainable according to the process to a salt or the conversion of a salt of a compound of the formula II obtainable according to the process to the free compound of the formula II or to another salt.

Suitable cyanides are sodium cyanide, potassium cyanide, trimethylsilyl cyanide and acetone cyanohydrin.

The general method for the reaction of carbonyl compounds, for example of the formula IV, with cyanides and amines, for example of the formula $R_6$—$NH_2$, is known as a Strecker reaction, for example in Organic Synthesis Coll. Vol. 3, 88 (1973).

Salts of compounds I can be prepared in a way known per se. Thus, for example, acid addition salts of compound I are obtained by treatment with a suitable acid or a suitable ion-exchange reagent and salts with bases are obtained by treatment with a suitable base or a suitable ion-exchange reagent.

Salts of compounds I can be converted in the usual way to the free compounds I, acid addition salts, e.g. by treatment with a suitable basic agent or a suitable ion exchange reagent, and salts with bases, e.g. by treatment with a suitable acid or a suitable ion-exchange reagent.

Salts of compounds I can be changed in a way known per se to other salts of compounds I, acid addition salts for example to other acid addition salts, e.g. by treatment of a salt of an inorganic acid, such as a hydrochloride, with a suitable metal salt, such as a sodium, barium or silver salt, of an acid, e.g. with silver acetate, in a suitable solvent, in which an inorganic salt, e.g. silver chloride, being formed is insoluble and for this reason precipitates from the reaction mixture.

According to the method or reaction conditions, the compounds I with salt forming properties can be obtained in the free form or in the form of salts.

The compounds I can also be obtained in the form of their hydrates and/or can incorporate other solvents, which might, for example, be used in the crystallization of compounds existing in the solid form.

The compounds I can exist as optical and/or geometrical isomers or mixtures thereof. The invention relates both to the pure isomers and to all possible mixtures of isomers and is to be correspondingly understood in each case heretofore and hereinafter, even if stereochemical details are not specifically referred to in every case.

Mixtures of diastereoisomers and mixtures of racemates of compounds I obtainable according to the process —depending on the choice of the starting materials and operating methods —or otherwise obtainable can be separated in a known way into the pure diastereoisomers or racemates on the basis of the physicochemical differences of the components, for example by fractional crystallization, distillation and/or chromatography.

Correspondingly obtainable mixtures of enantiomers, such as racemates, can be resolved into the optical isomers by known methods, for example by recrystallization from an optically active solvent, by chromatography on chiral adsorbents, e.g. high performance liquid chromatography (HPLC) on acetylcellulose, with the help of suitable microorganisms, by cleavage with specific immobilized enzymes, via the formation of inclusion complexes, e.g. by using chiral crown ethers, in which only one enantiomer is complexed.

In addition to through separation of the corresponding mixtures of isomers, pure diastereoisomers or enantiomers according to the invention can also be obtained through generally known methods of diastereoselective or enantioselective synthesis, e.g. by carrying out the process according to the invention with educts with correspondingly suitable stereochemistry.

Advantageously, the biologically most effective isomer, e.g. enantiomer, or mixture of isomers, e.g. mixture of enantiomers, is isolated or synthesized each time, provided that the individual components have different biological activity.

In the process of the present invention, use is preferably made of such starting materials and intermediates which result in the compounds I described at the beginning as particularly valuable.

The invention relates in particular to the preparation process described in the examples.

Starting materials and intermediates used according to the invention for the preparation of the compounds I which are novel, their use and processes for their preparation likewise form a subject-matter of the invention.

The compounds I according to the invention are characterized by a particularly broad activity spectrum and are valuable active ingredients in the field of pest control which are well tolerated by warm-blooded species, fish and plants, including in particular for controlling endo- and ecto parasites which parasitize animals.

In the context of the present invention, the term "ectoparasites" is understood to mean, in particular, insects, mites and ticks. This includes insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, reference may in particular be made to ectoparasites which are a nuisance to man or animals and which transmit pathogens, for example flies, such as *Musca domestica, Musca vetustissima, Musca autumnalis, Fannia canicularis, Sarcophaga camaria, Lucilia cuprina, Hypoderma bovis, Hypoderma lineatum, Chrysomyla chloropyga, Dermatobia hominis, Cochliomyia hominivorax, Gasterophilus intestinalis, Oestrus ovis, Stomoxys calcitrans, Haematobia irritans*, and mosquitoes (*Nematocera*), such as *Culicidae, Simullidae, Psychodidae*, but also bloodsucking parasites, for example fleas, such as *Ctenocephalides felis* and *Ctenocephalides canis* (cat and dog fleas), *Xenopsylla cheopis, Pulex irritans, Dermatophilus penetrans*, lice, such as *Damalina ovis, Pediculus humanis*, stable flies and horse flies (*Tabanidae*), *Haematopota* spp., such as *Haematopota pluvlalis, Tabamidea* spp., such as *Tabanus nigrovittatus, Chrysopsinae* spp., such as *Chrysops caecutiens*, tsetse flies, such as *Glossinia* species, biting insects, in particular cockroaches, such as *Blatella germanica, Blatta orientalls, Periplaneta americana*, mites, such as *Dermanyssus gallinae, Sarcoptes scabiei, Psoroptes ovis* and *Psorergates* spp., and last but not least ticks. The latter belong to the order *Acarina*. Known representatives of ticks are, e.g., *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals, including farm animals, such as cows, pigs, sheep and goats, poultry, such as chickens, turkeys and geese, fur-bearing animals, such as mink, foxes, chinchillas, rabbits and the like, and pets, such as cats and dogs, but also man.

The compounds I according to the invention are also effective against all or individual development stages of normally sensitive but also of resistant animal pests, such as insects and representatives of the order Acarina. The insecticidal, ovicidal and/or acaricidal action of the active ingredients according to the invention may in the process be displayed directly, i.e. in killing the pests, immediately or only after some time, for example during moulting, or their eggs, or indirectly, e.g. in reduced egg laying and/or in a reduced hatching rate, in which the good action corresponds to a kill rate (mortality) of at least 50 to 60%.

The compounds I can also be used against hygiene pests, in particular of the order Diptera with the families Sarcophagidae, Anophilidae and Culicidae; of the orders Orthoptera, Dictyoptera (e.g. the family Blattidae) and Hymenoptera (e.g. the family Formicidae).

The compounds I also have lasting activity in the case of phytoparasitic mites and insects. In the case of spider mites of the order Acarina, they are active against eggs, nymphs and adults of Tetranychidae (*Tetranychus* spp. and *Panonychus* spp.).

They are highly active in the case of the sucking insects of the order Homoptera, in particular against pests of the families Aphididae, Delphacidae, Cicadellidae, Psyllidae, Loccidae, Diaspididae and Erlophydidae (e.g. citrus rust mite); of the orders Hemiptera, Heteroptera and Thysanoptera, and in the case of the phytophagous insects of the orders Lepidoptera, Coleoptera, Diptera and Orthoptera.

They are also suitable as soil insecticides against pests in the soil.

The compounds of the formula I are accordingly active against all development stages of sucking and feeding insects on crops such as cereals, cotton, rice, maize, soya beans, potatoes, vegetables, fruit, tobacco, hops, citrus fruit, avocados and others.

The compounds of the formula I are also active against plant nematodes of the genera *Meloidogyne, Heterodera, Pratylenchus, Ditylenchus, Radopholus, Rizoglyphus* and others.

The compounds are particularly active against helminths, among which the endoparasitic nematodes and trematodes can be the cause of serious diseases in mammals and poultry, e.g. in sheep, pigs, goats, cattle, horses, donkeys, dogs, cats, guinea pigs and ornamental birds. Typical nematodes of this indication are: *Haemonchus, Trichostrongylusl, Ostertagia, Nematodirus, Cooperia, Ascaris, Bunostonum, Oesophagostonum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Mention may specifically be made, among the trematodes, of the family of the Fasciolideae, in particular *Fasciola hepatica*. The particular advantage of the compounds of the formula I is their activity against such parasites, which are resistant to benzimidazole-based active ingredients.

Certain species of the genera *Nematodirus, Cooperla* and *Oesophagostonum* attack the intestinal tract of the host animal, while others of the genera *Haemonchus* and *Ostertagia* parasitize in the stomach and others of the genus *Dictyocaulus* parasitize in lung tissue. Parasites of the families Filariidae and Setariidae are found in internal cell tissue and in organs, e.g. the heart, blood vessels, lymph vessels and subcutaneous tissue. Mention may particularly be made here of the dog heartworm, *Dirofilarla immitis*. The compounds of the formula I are highly effective against these parasites.

The pests which can be controlled with the compounds of the formula I also include, from the class Cestoda (tapeworms), the families Mesocestoidae, in particular the genus *Mesocestoides*, especially *M. lineatus; Dilepididae*, in particular *Dipylidium caninum, Joyeuxiella* spp., especially *Joyeuxiella pasquali*, and *Diplopylidium* spp.; and *Taeniidae*, in particular *Taenia pisiformis, Taenia cervi, Taenia ovis, Tanela hydatigena, Taenia multiceps, Taenia taeniaeformis, Taenia serialis* and *Echinocuccus* spp., particularly preferably *Taneia hydatigena, Taenia ovis, Taenia multiceps, Taenia serialis; Echinocuccus granulosus* and *Echinococcus granulosus* and *Echinococcus multilocularis*, and *Multiceps multiceps*.

In a very particularly preferred way, *Taenia hydatigena, T. pisiformis, T. ovis, T. taeniae-formis, Multiceps multiceps, Joyeuxiella pasquali, Dlpylidium caninum, Mesocestoides* spp., *Echinococcus granulosus* and *E. multilocularis* are controlled simultaneously with *Dirofilaria immitis, Ancylostoma* spp., *Toxocara* spp. and/or *Trichuris vulpis* on or in dogs and cats. Also in a preferred way, *Ctenocephalides felis* and/or *C. canis* are controlled simultaneously with the abovementioned nematodes and cestodes.

The compounds of the formula I are also suitable for controlling parasites which are pathogenic to man, among which may be mentioned, as typical representatives occurring in the digestive tract, those of the genera *Ancylostoma, Necator, Ascaris, Strongyloides, Trichinella, Capillaria, Trichuris* and *Enterobius*. The compounds of the present invention are also active against parasites of the genera *Wuchereria, Brugia, Onchocerca* and *Loa* from the family of the Filariidae, which occur in the blood, in tissue and in various organs, and also against Dracunculus and parasites of the genera *Strongyloldes* and *Trichinella*, which specifically infect the gastrointestinal tract.

In addition, the compounds of the formula I are also active against harmful fungi which cause disease in plants and in man and animals.

The good pesticidal action of the compounds of the formula I according to the invention corresponds to a kill rate (mortality) of at least 50–60% of the pests mentioned. In particular, the compounds of the formula I are characterized by an extraordinarily long duration of action.

The compounds of the formula I are used as such or preferably together with the auxiliaries conventional in formulation technology and can accordingly be processed in a known way, for example to emulsifiable concentrates, directly dilutable solutions, dilute emulsions, soluble powders, granules and also encapsulations in polymer substances. The application methods as well as the compositions are chosen in accordance with the intended aims and the prevailing circumstances.

The formulation, i.e. the compositions, preparations or combinations comprising the active ingredient of the formula I, or combinations of these active ingredients with other active ingredients, and, if desired, a solid or liquid additive, is prepared in a known way, for example by intimately mixing and/or grinding the active ingredients with extenders, for example with solvents, solid carriers and, if desired, surface-active compounds (surfactants).

The following are possible as solvents: alcohols, such as ethanol, propanol or butanol, and glycols, and their ethers and esters, such as propylene glycol, dipropylene glycol ether, ethylene glycol, ethylene glycol monomethyl ether or ethylene glycol monoethyl ether, ketones, such as cyclohexanone, isophorone or diacetone alcohol, strongly polar solvents, such as N-methyl-2-pyrrolidone, dimethyl sulfoxide, dimethylformamide or water, vegetable oils, such as rapeseed oil, castor oil, coconut oil or soybean oil; and, if desired, silicone oils.

Preferred application forms for use in warm-blooded animals for controlling helminths include solutions, emulsions, suspensions (drenches), feed additives, powders, tablets, including effervescent tablets, boluses, capsules, microencapsulations and pour-on formulations, care having to be taken over the physiological compatibility of the formulation auxiliaries.

Suitable binders for tablets and boluses are chemically modified polymeric natural products which are soluble in water or alcohol, such as starch, cellulose or protein derivatives (e.g., methylcellulose, carboxymethylcellulose, ethylhydroxyethylcellulose, proteins, such as zein, gelatin, and the like), and synthetic polymers, for example polyvinyl alcohol, polyvinylpyrrolidone, and the like. Tablets also comprise fillers (e.g., starch, microcrystalline cellulose, sugar, lactose, and the like), lubricants and disintegrating agents.

If the anthelmintic compositions are present In the form of feed concentrates, then high-performance feed, feed cereals or protein concentrates, for example, are used as carriers. Such feed concentrates or compositions can, in addition to the active ingredients, also comprise additives, vitamins, antibiotics, chemotherapeutics, or other pesticides, mainly bacteriostats, fungistats, coccidiostats, or also hormone preparations, anabolics or substances which promote growth, influence the quality of meat from animals for slaughter or are useful to the organism in another way. If the compositions or the active ingredients of the formula I present therein are added directly to the feed or to the drinking water for the animals, the finished feed or the finished drinking water comprises the active ingredients preferably in a concentration from approximately 0.0005 to 0.02% by weight (5–200 ppm).

The compounds of the formula I according to the invention can be used alone or in combination with other biocides. They can, e.g., be combined with pesticides possessing the same direction of action, in order to enhance the action, or can be combined with substances possessing another direction of action, in order to broaden the activity spectrum. It may also make sense to add substances which repel, known as repellents. If it is desired to expand the activity spectrum with regard to endoparasites, for example worms, the compounds of the formula I are appropriately combined with substances having endoparasiticidal properties. They can also, naturally, be used in combination with antibacterial compositions. Since the compounds of the formula I represent adulticides, i.e. since they are effective in particular against the adult stages of the target parasites, the addition of pesticides which are more likely to attack the juvenile stages of parasites can be highly advantageous. In this way, most of those parasites causing great economic damage are namely included. In addition, a substantial contribution is also made as well to avoiding the formation of resistance. Some combinations can also lead to synergistic effects, i.e. that the total amount of active substance consumed can be reduced, which is desirable from an ecological viewpoint. Preferred groups of combination participants and particularly preferred combination participants are mentioned subsequently, which combinations can, in addition to a compound of the formula I, comprise one or more of these participants.

Suitable participants in the mixture include biocides, for example the insecticides and acaricides with different mechanisms of action mentioned subsequently and sufficiently known to a person skilled in the art, for example chitin synthesis inhibitors, growth regulators; active ingredients which act as juvenile hormones; active ingredients which act as adulticides; broad spectrum insecticides, broad spectrum acaricides and nematicides; but also the sufficiently known anthelmintics and substances which repel insects and/or members of the *Acarina*, known as repellents or detachers.

Nonlimiting examples of suitable insecticides and acaricides are:

1. Abamectin
2. AC 303 630
3. Acephate
4. Acrinathrin
5. Alanycarb
6. Aldicarb
7. α-Cypermethrin
8. Alphamethrin
9. Amitraz
10. Avermectin $B_1$
11. AZ 60541
12. Azinphos E
13. Azinphos-methyl
14. Azocyclotin
15. *Bacillus subtil.* toxin
16. Bendiocarb
17. Benfuracarb
18. Bensultap
19. β-Cyfluthrin
20. Bifenthrin
21. BPMC
22. Brofenprox
23. Bromophos E
24. Bufencarb
25. Buprofezin
26. Butocarboxim
27. Butylpyridaben
28. Cadusafos
29. Carbaryl
30. Carbofuran
31. Carbophenothion
32. Cartap
33. Cloethocarb
34. Chlorethoxyfos
35. Chlorfenapyr
36. Chlorfluazuron
37. Chlormephos
38. Chlorpyrifos
39. Cis-Resmethrin
40. Clocythrin
41. Clofentezine
42. Cyanophos
43. Cycloprothrin
44. Cyfluthrin
45. Cyhexatin
46. D 2341
47. Deltamethrin
48. Demeton M
49. Demeton S
50. Demeton-S-methyl
51. Dibutylaminothio
52. Dichlofenthion
53. Dicliphos
54. Diethion
55. Diflubenzuron
56. Dimethoate
57. Dimethylvinphos
58. Dioxathion
59. DPX-MP062
60. Edifenphos
61. Emamectin
62. Endosulfan
63. Esfenvalerate
64. Ethiofencarb
65. Ethion
66. Ethofenprox
67. Ethoprophos
68. Etrimphos
69. Fenamiphos
70. Fenazaquin
71. Fenbutatin oxide
72. Fenitrothion -continued 73. Fenobucarb
74. Fenothiocarb
75. Fenoxycarb
76. Fenpropathrin
77. Fenpyrad
78. Fenpyroximate
79. Fenthion
80. Fenvalerate
81. Fipronil
82. Fluazinam
83. Fluazuron
84. Flucycloxuron
85. Flucythrinate
86. Flufenoxuron
87. Flufenprox
88. Fonophos
89. Formothion
90. Fosthiazate
91. Fubfenprox
92. HCH
93. Heptenophos
94. Hexaflumuron
95. Hexythiazox
96. Hydroprene
97. Imidacloprid
98. Insect-active fungi
99. Insect-active nematodes
100. Insect-active viruses
101. Iprobenfos
102. Isofenphos
103. Isoprocarb
104. Isoxathion
105. Ivermectin
106. λ-Cyhalothrin
107. Lufenuron
108. Malathion
109. Mecarbam
110. Mesulfenphos
111. Metaldehyde
112. Methamidophos
113. Methiocarb
114. Methomyl
115. Methoprene
116. Metolcarb
117. Mevinphos
118. Milbemectin
119. Moxidectin
120. Naled
121. NC 184
122. NI-25, Acetamiprid
123. Nitenpyram
124. Omethoate
125. Oxamyl
126. Oxydemeton M
127. Oxydeprofos
128. Parathion
129. Parathion-methyl
130. Permethrin
131. Phenthoate
132. Phorate
133. Phosalone
134. Phosmet
135. Phoxim
136. Pirimicarb
137. Pirimiphos E
138. Pirimiphos M
139. Promecarb
140. Propaphos
141. Propoxur
142. Prothiofos
143. Prothoate
144. Pyraclophos
145. Pyradaphenthion
146. Pyresmethrin
147. Pyrethrum
148. Pyridaben
149. Pyrimidifen -continued 150. Pyriproxyfen
151. RH-5992
152. RH-2485
153. Salithion
154. Sebufos
155. Silafluofen
156. Spinosad
157. Sulfotep
158. Sulprofos
159. Tebufenozide
160. Tebufenpyrad
161. Tebupirimphos
162. Teflubenzuron
163. Tefluthrin
164. Temephos
165. Terbam
166. Terbufos
167. Tetrachlorvinphos
168. Thiafenox
169. Thiodicarb
170. Thiofanox
171. Thionazin
172. Thuringiensin
173. Tralomethrin
174. Triarthene
175. Triazamate
176. Triazophos
177. Triazuron
178. Trichlorfon
179. Triflumuron
180. Trimethacarb
181. Vamidothion
182. XMC (3,5-xylyl methylcarbamate)
183. Xylylcarb
184. YI 5301/5302
185. ζ-Cypermethrin
186. Zetamethrin Nonlimiting examples of suitable anthelmintics are mentioned subsequently, in which some representatives, in addition to the anthelmintic activity, also have an insecticidal and acaricidal activity and are already included in the above list:

(A1) Praziquantel=2-Cyclohexylcarbonyl-4-oxo-1,2,3,6,7,11 b-hexahydro-4H-pyrazino[2,1-α]isoquinoline (A2) Closantel=3,5-Diiodo-N-[5-chloro-2-methyl-4-(α-cyano4-chlorobenzyl)phenyl]-salicylamide (A3) Triclabendazole=5-Chloro-6-(2,3-dichlorophenoxy)-2-methylthio-1H-benzimidazole (A4) Levamisole=L-(−)-2,3,5,6-Tetrahydro-6-phenylimidazo[2,1-b]thiazole (A5) Mebendazole=Methyl 5-benzoyl-1H-benzimidazol-2-ylcarbamate (A6) Omphalotin=a macrocyclic fermentation product from the fungus *Omphalotus oleanius* disclosed in WO 97/20857

(A7) Abamectin=Avermectin B1

(A8) Ivermectin=22,23-Dihydroavermectin B1

(A9) Moxidectin=5-O-Demethyl-28-deoxy-25-(1,3-dimethyl-1-butenyl)-6,28-epoxy-23-(methoxyimino)milbemycin B (A10) Doramectin=25-Cyclohexyl-5-O-demethyl-25-de(1-methylpropyl)avermectin Ala (A11) Milbemectin=Mixture of Milbemycin A3 and Milbemycin A4

(A12) Milbemycin oxime=5-Oxime of Milbemectin

Nonlimiting examples of suitable repelling substances (repellents or detachers) are:

(R1) DEET (N,N-Diethyl-m-toluamide)

(R2) KBR 3023 N-Butyl-2-oxycarbonyl-2-(2-hydroxyethyl) piperidine (R3) Cymlazole =N-2,3-Dihydro-3-methyl-1,3-thiazol-2-ylidene-2,4-xylidine The participants in the mixture which are mentioned are very well known to a person skilled in the art. Most are described in the various editions of The Pesticide Manual, The British Crop Protection Council, London, others in the various editions of The Merck Index, Merck & Co. Inc., Rahway, N.J., USA, or in the patent literature. The following listing is accordingly restricted to a few references by way of examples.

(I) 2-Methyl-2-(methylthio)propionaldehyde O-methylcarbamoyloxime (Aldicarb), from The Pesticide Manual, 11$_{th}$ Ed. (1997), The British Crop Protection Council, London, page 26;

(II) S-(3,4-Dihydro-4-oxobenzo[d][1,2,3]triazin-3-ylmethyl) O,O-dimethyl phosphorodithioate (Azinphos-methyl), from The Pesticide Manual, 11$^{th}$ Ed. (1997), The British Crop Protection Council, London, page 67;

(III) Ethyl N-[2,3-dihydro-2,2-dimethylbenzofuran-7-yloxycarbonyl(methyl)aminothio]-N-isopropyl-β-alaninate (Benfuracarb), from The Pesticide Manual, 11$^{th}$ Ed. (1997), The British Crop Protection Council, London, page 96;

(IV) 2-Methylbiphenyl-3-ylmethyl (Z)-(1RS)-cis-3-(2-chloro-3,3,3-trifluoroprop-1-enyl)2,2-dimethylcyclopropanecarboxylate (Bifenthrin), from The Pesticide Manual, 11$^{th}$ Ed. (1997), The British Crop Protection Council, London, page 118;

(V) 2-tert-Butylimino-3-isopropyl-5-phenyl-1,3,5-thiadiazinan4-one (Buprofezin), from The Pesticide Manual, 11$^{th}$ Ed. (1997), The British Crop Protection Council; London, page 157;

(VI) 2,3-Dihydro-2,2-dimethylbenzofuran-7-yl methylcarbamate (Carbofuran), from The Pesticide Manual, 11$^{th}$ Ed. (1997), The British Crop Protection Council, London, page 186;

(VII) 2,3-Dihydro-2,2-dimethylbenzofuran-7-yl (dibutylaminothio)methylcarbamate (Carbosulfan), from The Pesticide Manual, 11$^{th}$ Ed. (1997), The British Crop Protection Council, London, page 188;

(VIII) S,S'-(2-Dimethylaminotrimethylene) bis(thiocarbamate) (Cartap), from The Pesticide Manual, 11$^{th}$ Ed. (1997), The British Crop Protection Council, London, page 193;

(IX) 1-[3,5-Dichloro-4-(3-chloro-5-trifluoromethyl-2-pyridyloxy)phenyl]-3-(2,6-difluorobenzoyl)-urea (Chlorfluazuron), from The Pesticide Manual, 11$^{th}$ Ed. (1997), The British Crop Protection Council, London, page 213;

(X) O,O-Diethyl O-3,5,6-trichloro-2-pyridyl phosphorothioate (Chlorpyrifos), from The Pesticide Manual, 11$^{th}$ Ed. (1997), The British Crop Protection Council, London, page 235;

(XI) (RS)-α-Cyano-4-fluoro-3-phenoxybenzyl (1RS,3RS,1 RS,3RS)-3-(2,2-dichlorovinyl)-2,2-di-methylcyclopropanecarboxylate (Cyfluthrin), from The Pesticide Manual, 11$^{th}$ Ed. (1997), The British Crop Protection Council, London, page 293;

(XII) Mixture of (S)-α-cyano-3-phenoxybenzyl (4)-(1R,3R)-3-(2-chloro-3,3,3-trifluoro-propenyl)-2,2-dimethylcyclopropanecarboxylate and (R)-α-cyano-3-phenoxybenzyl (Z)-(1S,3S)-3-(2-chloro-3,3,3-trifluoropropenyl)-2,2-dimethylcyclopropanecarboxylate (Lambda-Cyhalothrin), from The Pesticide Manual, 11$^{th}$ Ed. (1997), The British Crop Protection Council, London, page 300;

(XIII) Racemate consisting of (S)-αcyano-3-phenoxybenzyl (1R,3R)-3-(2,2-dichlorovinyl)-2,2-dimethylcyclopropanecarboxylate and (R)-α-cyano-3-phenoxybenzyl(1S,3S)-3-(2,2-dichlorovinyl)-2,2-dimethylcyclopropanecarboxylate (Alpha-cypermethrin), from The Pesticide Manual, 11$^{th}$ Ed. (1997), The British Crop Protection Council, London, page 308;

(XIV) A mixture of the stereoisomers of (S)-α-cyano-3-phenoxybenzyl (1RS,3RS,1 RS,3RS)-3-(2,2-dichlorovinyl)-2,2-dimethylcyclopropanecarboxylate (zeta-Cypermethrin), from The Pesticide Manual, 11$^{th}$ Ed. (1997), The British Crop Protection Council, London, page 314;

(XV) (S)-α-Cyano-3-phenoxybenzyl (1R,3R)-3-(2,2-dibromovinyl)-2,2-dimethylcyclopropane-carboxylate (Deltamethrin), from The Pesticide Manual, 11$^{th}$ Ed. (1997), The British Crop Protection Council, London, page 344;

(XVI) 1-(4-Chlorophenyl)-3-(2,6-difluorobenzoyl)urea (Diflubenzuron), from The Pesticide Manual, 11$^{th}$ Ed. (1997), The British Crop Protection Council, London, page 395;

(XVII) (1,4,5,6,7,7-Hexachloro-8,9,10-trinorbom-5-en-2,3-ylenebismethylene)sulfite (Endosulfan), from The Pesticide Manual, 11$^{th}$ Ed. (1997), The British Crop Protection Council, London, page 459;

(XVIII) α-Ethylthio-o-tolyl methylcarbamate (Ethiofencarb), from The Pesticide Manual, 11$^{th}$ Ed. (1997), The British Crop Protection Council, London, page 479;

(XIX) O,O-Dimethyl 04-nitro-m-tolyl phosphorothioate (Fenitrothion), from The Pesticide Manual, 11$^{th}$ Ed. (1997), The British Crop Protection Council, London, page 514;

(XX) 2-sec-Butylphenyl methylcarbamate (Fenobucarb), from The Pesticide Manual, 11$^{th}$ Ed. (1997), The British Crop Protection Council, London, page 516;

(XXI) (RS)-α-Cyano-3-phenoxybenzyl (RS)-2-(4-chlorophenyl)-3-methylbutyrate (Fenvalerate), from The Pesticide Manual, 11$^{th}$ Ed. (1997), The British Crop Protection Council, London, page 539;

(XXII) S-[Formyl(methyl)carbamoylmethyl]O,O-dimethyl phosphorodithloate (Formothion), from The Pesticide Manual, 11$^{th}$ Ed. (1997), The British Crop Protection Council, London, page 625;

(XXIII) 4-Methylthio-3,5-xylyl methylcarbamate (Methlocarb), from The Pesticide Manual, 11$^{th}$ Ed. (1997), The British Crop Protection Council, London, page 813;

(XXIV) 7-Chlorobicyclo[3.2.0]hepta-2,6-dien-6-yl dimethyl phosphate (Heptenophos), from The Pesticide Manual, 11$^{th}$ Ed. (1997), The British Crop Protection Council, London, page 670;

(XXV) 1-(6-Chloro-3-pyridylmethyl)-nitroimidazolidin-2-ylideneamine (Imidacloprid), from The Pesticide Manual, 11$^{th}$ Ed. (1997), The British Crop Protection Council, London, page 706;

(XXVI) 2-Isopropylphenyl methylcarbamate (Isoprocarb), from The Pesticide Manual, 11$^{th}$ Ed. (1997), The British Crop Protection Council, London, page 729;

(XXVII) O,S-Dimethyl phosphoramidothioate (Methamidophos), from The Pesticide Manual, 11$^{th}$ Ed. (1997), The British Crop Protection Council, London, page 808;

(XXVIII) S-Methyl N-(methylcarbamoyloxy)thioacetimidate (Methomyl), from The Pesticide Manual, 11$^{th}$ Ed. (1997), The British Crop Protection Council, London, page 815;

(XXIX) Methyl 3-(dimethoxyphosphinoyloxy)but-2-enoate (Mevinphos), from The Pesticide Manual, 11$^{th}$ Ed. (1997), The British Crop Protection Council, London, page 844;

(XXX) O,O-Diethyl 0-4-nitrophenyl phosphorothioate (Parathion), from The Pesticide Manual, 11$^{th}$ Ed. (1997), The British Crop Protection Council, London, page 926;

(XXXI) O,O-Dimethyl 0-4-nitrophenyl phosphorothioate (Parathion-methyl), from The Pesticide Manual, 11th Ed. (1997), The British Crop Protection Council, London, page 928;

(XXXII) S-6-Chloro-2,3-dihydro-2-oxo-1,3-benzoxazol-3-ylmethyl O,O-diethyl phosphoro-dithioate (Phosalone), from The Pesticide Manual, 11th Ed. (1997), The British Crop Protection Council, London, page 963;

(XXXIII) 2-Dimethylamino-5,6-dimethylpyrimidin-4-yl dimethylcarbamate (Pirimicarb), from The Pesticide Manual, 11th Ed. (1997), The British Crop Protection Council, London, page 985;

(XXXIV) 2-Isopropoxyphenyl methylcarbamate (Propoxur), from The Pesticide Manual, 11th Ed. (1997), The British Crop Protection Council, London, page 1036;

(XXXV) 1-(3,5-Dichloro-2,4-difluorophenyl)-3-(2,6-difluorobenzoyl)urea (Teflubenzuron), from The Pesticide Manual, 11th Ed. (1997), The British Crop Protection Council, London, page 1158;

(XXXVI) S-tert-Butylthiomethyl O,O-diethyl phosphorodithioate (Terbufos), from The Pesticide Manual, 11th Ed. (1997), The British Crop Protection Council, London, page 1165;

(XXXVII) Ethyl (3-tert-butyl-1-dimethylcarbamoyl-1H-1,2,4-triazol-5-ylthio)acetate, (Triazamate), from The Pesticide Manual, 11th Ed. (1997), The British Crop Protection Council, London, page 1224;

(XXXVIII) Abamectin, from The Pesticide Manual, 11th Ed. (1997), The British Crop Protection Council, London, page 3;

(XXXIX) 2-sec-Butylphenyl methylcarbamate (Fenobucarb), from The Pesticide Manual, 11th Ed. (1997), The British Crop Protection Council, London, page 516;

(XL) N-tert-Butyl-N'-(4-ethylbenzoyl)-3,5-dimethylbenzohydrazide (Tebufenozide), from The Pesticide Manual, 11th Ed. (1997), The British Crop Protection Council, London, page 1147;

(XLI) (±)-5-Amino-1-(2,6-dichloro-$\alpha,\alpha,\alpha$-trifluoro-p-tolyl)-4-trifluoromethylsulfinylpyrazole-3-carbonitrile (Fipronil), from The Pesticide Manual, 11th Ed. (1997), The British Crop Protection Council, London, page 545;

(XLII) (RS)-$\alpha$-Cyano-4-fluoro-3-phenoxybenzyl (1RS, 3RS;1 RS,3SR)$_3$-(2,2-dichlorovinyl)-2,2-dimethylcyclopropanecarboxylate (beta-Cyfluthrin), from The Pesticide Manual, 11th Ed. (1997), The British Crop Protection Council, London, page 295;

(XLIII) (4-Ethoxyphenyl)[3-(4-fluoro-3-phenoxyphenyl)propyl](dimethyl)silane (Silafluofen), from The Pesticide Manual, 11th Ed. (1997), The British Crop Protection Council, London, page 1105;

(XLIV) tert-Butyl (E)-$\alpha$-(1,3-dimethyl-5-phenoxypyrazol-4-ylmethyleneamino-oxy)-p-toluate (Fenpyroximate), from The Pesticide Manual, 11th Ed. (1997), The British Crop Protection Council, London, page 530;

(XLV) 2-tert-Butyl-5-(4-tert-butylbenzylthio)-4-chloropyridazin-3(2H)-one (Pyridaben), from The Pesticide Manual, 11th Ed. (1997), The British Crop Protection Council, London, page 1161;

(XLVI) 4-[[4-(1,1-Dimethylethyl)phenyl]ethoxy]quinazoline (Fenazaquin), from The Pesticide Manual, 11th Ed. (1997), The British Crop Protection Council, London, page 507;

(XLVII) 4-Phenoxyphenyl (RS)-2-(2-pyridyloxy)propyl ether (Pyriproxyfen), from The Pesticide Manual, 11th Ed. (1997), The British Crop Protection Council, London, page 1073;

(XLVIII) 5-Chloro-1H2-[4-(2-ethoxyethyl)-2,3-dimethylphenoxy]ethyl)-6-ethylpyrimidin-4-amine (Pyrimidifen), from The Pesticide Manual, 11th Ed. (1997), The British Crop Protection Council, London, page 1070;

(XLIX) (E)-N-(6-Chloro-3-pyridylmethyl)-N-ethyl-N-methyl-2-nitrovinylidenediamine (Nitenpyram), from The Pesticide Manual, 11th Ed. (1997), The British Crop Protection Council, London, page 880;

(L) (E)-$N^1$-[(6-Chloro-3-pyridyl)methyl]-$N^2$-cyano-$N^1$-methylacetamidine (NI-25, Acetamiprid), from The Pesticide Manual, 11th Ed. (1997), The British Crop Protection Council, London, page 9;

(LI) Avermectin $B_1$, from The Pesticide Manual, 11th Ed. (1997), The British Crop Protection Council, London, page 3;

(LII) An insect-active extract from a plant, in particular (2R,6aS,12aS)-1,2,6,6a,12,12a-hexahydro-2-isopropenyl-8,9-dimethoxychromeno[3,4-b]furo[2,3-h]chromen-6-one (Rotenone), from The Pesticide Manual, 11th Ed. (1997), The British Crop Protection Council, London, page 1097; and an extract from Azadirachta indica, in particular azadirachtin, from The Pesticide Manual, 11th Ed. (1997), The British Crop Protection Council, London, page 59;

(LII) A preparation comprising insect-active nematodes, preferably Heterorhabditis bacteriophora and Heterorhabditis megidis, from The Pesticide Manual, 11th Ed. (1997), The British Crop Protection Council, London, page 671; Steinernema feltiae, from The Pesticide Manual, 11th Ed. (1997), The British Crop Protection Council, London, page 1115, and Steinernema scapterisci, from The Pesticide Manual, 11th Ed. (1997), The British Crop Protection Council, London, page 1116;

(LIV) A preparation obtainable from Bacillus subtills, from The Pesticide Manual, 11th Ed. (1997), The British Crop Protection Council, London, page 72; or from a Bacillus thuringlensis strain except for compounds isolated from GC91 or from NCTC11821; The Pesticide Manual, 11th Ed. (1997), The British Crop Protection Council, London, page 73;

(LV) A preparation comprising insect-active fungi, preferably Verticillium lecanil, from The Pesticide Manual, 11th Ed. (1997), The British Crop Protection Council, London, page 1266; Beauveria brogniartil, from The Pesticide Manual, 11th Ed. (1997), The British Crop Protection Council, London, page 85; and Beauvera bassiana, from The Pesticide Manual, 11th Ed. (1997), The British Crop Protection Council, London, page 83;

(LVI) A preparation comprising insect-active viruses, preferably Neodipridon Sertifer NPV, from The Pesticide Manual, 11th Ed. (1997), The British Crop Protection Council, London, page 1342; Mamestra brassicae NPV, from The Pesticide Manual, 11th Ed. (1997), The British Crop Protection Council, London, page 759; and Cydia pomonella granulosis virus, from The Pesticide Manual, 11th Ed. (1997), The British Crop Protection Council, London, page 291;

(CLXXXI) Methyl 7-chloro-2,3,4a,5-tetrahydro-2-[methoxycarbonyl(4-trifluoromethoxy-phenyl)carbamoyl]indol[1,2-e]oxazoline-4a-carboxylate (DPX-MP062, Indoxacarb), from The Pesticide Manual, 11th Ed. (1997), The British Crop Protection Council, London, page 453;

(CLXXXII) N'-tert-Butyl-N'(3,5-dimethylbenzoyl)-3-methoxy-2-methylbenzohydrazide (RH-2485, Methoxyfenozide), from The Pesticide Manual, 11th Ed. (1997), The British Crop Protection Council, London, page 1094;

(CLXXXIII) isopropyl N'-[4-methoxybiphenyl-3-yl]hydrazinecarboxylate (D 2341), from Brighton Crop Protection Conference, 1996, 487–493; and (R2) Book of Abstracts, 212th ACS National Meeting, Orlando, Fla., August 25–29 (1996), AGRO-020. Publisher: American Chemical Society, Washington, D.C. CONEN: 63BFAF.

According to what has been said above, a further essential aspect of the present invention relates to combination preparations for the control of parasites in warm-blooded animals, which comprise, in addition to a compound of the formula I, at least one further active ingredient with an identical or different direction of action and at least one physiologically compatible carrier. The present invention is not restricted to combinations of two.

The anthelmintic compositions according to the invention generally comprise 0.1 to 99% by weight, in particular 0.1 to 95% by weight, of active ingredient of the formula I or mixtures thereof, and 99.9 to 1% by weight, in particular 99.8 to 5% by weight, of a solid or liquid additive, including 0 to 25% by weight, in particular 0.1 to 25% by weight, of a surfactant.

The compositions according to the invention can be applied topically, perorally, parenterally or subcutaneously to the animals to be treated, the compositions being present in the form of solutions, emulsions, suspensions (drenches), powders, tablets, boluses, capsules and as pour-on formulations.

The pour-on or spot-on method consists in applying the compound of the formula I to a locally restricted part of the skin or fur, advantageously on the neck or back of the animal. This is carried out, e.g., by applying a spot or dash of the pour-on or spot-on formulation to a relatively small area of the fur, from where the active substance spreads out virtually unaided over wide regions of the fur because of the spreading components of the formulation and supported by the movements of the animal.

It is advantageous for pour-on or spot-on formulations to comprise carriers which promote speedy distribution on the surface of the skin or in the fur of the host animal and which are generally described as spreading oils. Suitable carriers are, e.g., oily solutions; alcoholic and isopropanolic solutions, for example solutions of 2-octyldodecanol or oleyl alcohol; solutions in esters of monocarboxylic acids, such as isopropyl myristate, isopropyl palmitate, lauric acid oxal ester, oleyl oleate, decyl oleate, hexyl laurate, capric acid esters of saturated fatty alcohols with a chain length of $C_{12}$–$C_{18}$; solutions of esters of dicarboxylic acids, such as dibutyl phthalate, diisopropyl isophthalate, diisopropyl adipate or di(n-butyl) adipate, or also solutions of esters of aliphatic acids, e.g. glycols. It can be advantageous if a dispersant known from the pharmaceutical or cosmetics industry is additionally present. Examples are 2-pyrrolidone, 2-(N-alkyl)pyrrolidone, acetone, polyethylene glycol and ethers and esters thereof, propylene glycol or synthetic triglycerides.

The oily solutions include, e.g., vegetable oils, such as olive oil, groundnut oil, sesame oil, pine oil, linseed oil or castor oil. The vegetable oils can also be present in epoxidized form. Paraffin oils and silicone oils can also be used.

In general, a pour-on or spot-on formulation comprises 1 to 20% by weight of a compound of the formula I, 0.1 to 50% by weight of dispersant and 45 to 98.9% by weight of solvent.

The pour-on or spot-on method can be used particularly advantageously with gregarious animals, such as cattle, horses, sheep or pigs, where it is difficult or time-consuming to treat all the animals orally or via injection. Because of its simplicity, this method can naturally also be used with all other animals, including individual domestic animals or pets, and is very popular with animal owners because it can often be implemented without the expert assistance of a veterinary surgeon.

While concentrated compositions are more preferred as commercially available products, the end user generally uses dilute compositions.

Such compositions can comprise yet further additives, such as stabilizers, antifoaming agents, viscosity regulators, binders, deposit builders and other active ingredients to obtain specific effects.

Such anthelmintic compositions used by the end user likewise form part of the present invention.

In each of the methods according to the invention for controlling pests or of the pesticides according to the invention, the active ingredients of the formula I can be used in all their steric configurations or mixtures thereof.

The invention also includes a method for the prophylactic protection of warm-blooded animals, in particular of productive livestock, domestic animals and pets, against parasitic helminths, which comprises applying the active ingredients of the formula I or the active ingredient formulations prepared therefrom as a feed additive or drinking water additive or also in the solid or liquid form, orally, by injection or parenterally, to the animals. The invention also includes the compounds of the formula I according to the invention for use in one of the methods mentioned.

The following examples serve merely to illustrate the invention, without limiting it, the term "active ingredients" representing a substance listed in Table 1.

Preferred formulations are in particular composed in the following way:

(%=percent by weight)

FORMULATION EXAMPLES

| 1. Granules | a) | b) |
| --- | --- | --- |
| Active ingredient | 5% | 10% |
| Kaolin | 94% | — |
| Highly dispersed silica | 1% | — |
| Attapulgite | — | 90% |

The active ingredient is dissolved in methylene chloride and sprayed onto the carrier, and the solvent is subsequently evaporated under reduced pressure. Such granules can be added to the animal feed.

| 2. Granules | |
| --- | --- |
| Active ingredient | 3% |
| Polyethylene glycol (MW 200) | 3% |
| Kaolin | 94% |

(MW = molecular weight)

The finely milled active ingredient is applied evenly in a mixer to the kaolin, which has been moistened with polyethylene glycol. In this way, dust-free coated granules are obtained.

3. Tablets or Boluses

| | | |
|---|---|---|
| I | Active ingredient | 33.00% |
| | Methylcellulose | 0.80% |
| | Highly dispersed silica | 0.80% |
| | Maize starch | 8.40% |
| II | Cryst. lactose | 22.50% |
| | Maize starch | 17.00% |
| | Microcryst. cellulose | 16.50% |
| | Magnesium stearate | 1.00% |

I Methylcellulose is stirred into water. After the material has swollen, silica is stirred in and the mixture is homogeneously suspended. Active ingredient and maize starch are mixed. The aqueous suspension is incorporated in this mixture and kneaded to a dough. The substance thus obtained is granulated through a 12 M sieve and dried.

II All 4 auxiliaries are intimately mixed.

III The premixes obtained according to 1 and II are mixed and pressed to give tablets or boluses.

4. Injectables

A. Oily vehicle (slow release)

| | | |
|---|---|---|
| 1. | Active ingredient | 0.1–1.0 g |
| | Groundnut oil | ad 100 ml |
| 2. | Active ingredient | 0.1–1.0 g |
| | Sesame oil | ad 100 ml |

Preparation: The active ingredient is dissolved in a portion of the oil with stirring and, if desired, gentle heating, made up to the required volume after cooling and sterilely filtered through a suitable membrane filter with a size of 0.22 μm.

B. Water-miscible solvent (medium release rate)

| | | |
|---|---|---|
| 1. | Active ingredient | 0.1–1.0 g |
| | 4-Hydroxymethyl-1,3-dioxolane (glycerol formal) | 40 g |
| | 1,2-Propanediol | ad 100 ml |
| 2. | Active ingredient | 0.1–1.0 g |
| | Glycerol dimethyl acetal | 40 g |
| | 1,2-Propanediol | ad 100 ml |

Preparation: The active ingredient is dissolved in a portion of the solvent with stirring, made up to the required volume and sterilely filtered through a suitable membrane filter with a size of 0.22 μm.

C. Aqueous solubilisate (rapid release)

| | | |
|---|---|---|
| 1. | Active ingredient | 0.1–1.0 g |
| | Polyethoxylated castor oil (40 ethylene oxide units) | 10 g |
| | 1,2-Propanediol | 20 g |
| | Benzyl alcohol | 1 g |
| | Water for injections | ad 100 ml |
| 2. | Active Ingredient | 0.1–1.0 g |
| | Polyethoxylated sorbitan monooleate (20 ethylene oxide units) | 8 g |
| | 4-Hydroxymethyl-1,3-dioxolane (glycerol formal) | 20 g |
| | Benzyl alcohol | 1 g |
| | Water for injections | ad 100 ml |

Preparation: The active ingredient is dissolved in the solvents and the surfactant and made up to the required volume with water. Sterile filtration is carried out through a suitable membrane filter with a pore diameter of 0.22 μm.

5. Pour-on

| | | |
|---|---|---|
| A. | Active ingredient | 5 g |
| | Isopropyl myristate | 10 g |
| | Isopropanol | ad 100 ml |
| B. | Active ingredient | 2 g |
| | Hexyl laurate | 5 g |
| | Triglycerides of medium chain length | 15 g |
| | Ethanol | ad 100 ml |
| C. | Active ingredient | 2 g |
| | Oleyl oleate | 5 g |
| | N-Methylpyrrolidone | 40 g |
| | Isopropanol | ad 100 ml |

The aqueous systems can preferably also be used for oral and/or intraruminal administration.

The compositions can also comprise further additives, such as stabilizers, e.g. epoxidized or nonepoxidized vegetable oils (epoxidized coconut oil, rapeseed oil or soybean oil), antifoaming agents, e.g. silicone oil, preservatives, viscosity regulators, binders, deposit builders and fertilizers or other active ingredients to obtain specific effects.

Further biologically active substances or additives which are neutral towards the compounds of the formula I and have no adverse effect on the host animal to be treated, and mineral salts or vitamins, can also be added to the compositions described.

The following examples serve to clarify the invention. They do not limit the invention. The symbol 'h' denotes hour.

PREPARATION EXAMPLES

Example 1

4-(2-Trifluoromethylphenyl)-3-buten-2-one a) 4.29 g of N,O-dimethylhydroxylamine hydrochloride, 9.5 g of 2-trifluoromethylcinnamic acid, 11.36 g of ethyldiisopropylamine, 0.45 g of 4-dimethylaminopyridine and 8.43 g of N-(3-dimethylaminopropyl)-N'-ethylcarbodiimide hydrochloride are dissolved in 80 ml of methylene chloride and are stirred at ambient temperature under a nitrogen atmosphere for 8 h. The mixture is subsequently diluted with 200 ml of ethyl acetate and then washed twice with 1 N hydrochloric acid solution, then twice with a saturated sodium bicarbonate solution and finally once with saturated sodium chloride solution. The organic phase is separated, dried with magnesium sulfate and evaporated under reduced pressure. After purifying by flash chromatography, N-methoxy-N-methyl3-(2-trifluoromethylphenyl)acrylamide is thus obtained.

b) 11 g of N-methoxy-N-methyl-3-(2-trifluoromethylphenyl)acrylamide are dissolved in 150 ml of dry tetrahydrofuran under a nitrogen atmosphere, cooled to −78° C. and treated dropwise with 36 ml of a 1.4N solution of methyllithium in diethyl ether in 10 minutes. The solution is subsequently furthermore stirred at −78° C. for 2 h and then hydrolysed with water. 200 ml of ethyl acetate are now added at ambient temperature and the mixture is washed three times with saturated sodium chloride solution. The organic phase is finally separated, dried with magnesium sulfate and evaporated under reduced pressure. After purifying by flash chromatography, the title compound is thus obtained.

Example 2

4-(2-Trifluoromethylphenyl)butan-2-one 200 mg of Raney nickel are added to a solution of 2.05 g of 4-(2-trifluoromethylphenyl)-3-buten-2-one in 100 ml of ethyl acetate and the mixture is stirred under a hydrogen atmosphere and at standard pressure for 7 h. The mixture is subsequently filtered and the filtrate is evaporated under reduced pressure, whereby the title compound is obtained.

Example 3

2-Amino-2-methyl-4-(2-trifluoromethylphenyl)butyronitrile 1.5 g of 4-(2-trifluoromethylphenyl)butan-2-one, 0.41 g of sodium cyanide and 0.56 g of ammonium chloride are dissolved in 77 ml of a 2M solution of ammonia in ethanol and the mixture is stirred at ambient temperature for 7 h. The mixture is subsequently concentrated under reduced pressure and the residue is redissolved in ethyl acetate and washed with water and three times with saturated sodium chloride solution. The organic phase is separated, dried with magnesium sulfate and evaporated under reduced pressure. After purifying the residue by flash chromatography, the title compound is thus obtained.

Example 4

N-(1-cyano-1-methyl-3-[2-trifluoromethylphenyl] propyl)-4-trifluoromethoxy-benzamide 200 mg of 2-amino-2-methyl-4-(2-trifluoromethylphenyl) butyronitrile, 185 mg of 4-trifluoro-methoxybenzoyl chloride, 107 mg of ethyldiisopropylamine and 10 mg of 4-dimethylamino-pyridine are dissolved in 10 ml of methylene chloride and the mixture is stirred under a nitrogen atmosphere for 6 h. After the addition of 50 ml of ethyl acetate, the organic phase is washed once with water and then twice with saturated sodium chloride solution. The organic phase is separated, dried with magnesium sulfate and evaporated under reduced pressure. After purifying the residue by flash chromatography, the title compound is thus obtained as white crystals with a melting point of 87–9° C.

The substances mentioned in the following table can also be prepared analogously to the procedure described above. The melting point values are given in ° C.

TABLE 1

| No. | X | $R_9$ | $R_{10}$ | Phys. data |
|---|---|---|---|---|
| 1.1 | $CH_2CH_2$ | H | H | |
| 1.2 | $CH_2CH_2$ | H | 2-F | |
| 1.3 | $CH_2CH_2$ | H | 3-F | |
| 1.4 | $CH_2CH_2$ | H | 4-F | |
| 1.5 | $CH_2CH_2$ | H | 2-Cl | |
| 1.6 | $CH_2CH_2$ | H | 3-Cl | |
| 1.7 | $CH_2CH_2$ | H | 4-Cl | |
| 1.8 | $CH_2CH_2$ | H | 2-$CH_3$ | |
| 1.9 | $CH_2CH_2$ | H | 3-$CH_3$ | |
| 1.10 | $CH_2CH_2$ | H | 4-$CH_3$ | |
| 1.11 | $CH_2CH_2$ | H | 2-$CF_3$ | |
| 1.12 | $CH_2CH_2$ | H | 3-$CF_3$ | |
| 1.13 | $CH_2CH_2$ | H | 4-$CF_3$ | |
| 1.14 | $CH_2CH_2$ | H | 2-$OCF_3$ | |
| 1.15 | $CH_2CH_2$ | H | 3-$OCF_3$ | |
| 1.16 | $CH_2CH_2$ | H | 4-$OCF_3$ | M.p. 129° C. |
| 1.17 | $CH_2CH_2$ | H | 2-$OCF_2CF_2H$ | |
| 1.18 | $CH_2CH_2$ | H | 3-$OCF_2CF_2H$ | |
| 1.19 | $CH_2CH_2$ | H | 4-$OCF_2CF_2H$ | |
| 1.20 | $CH_2CH_2$ | H | 2-$OCF_2CF_3$ | |
| 1.21 | $CH_2CH_2$ | H | 3-$OCF_2CF_3$ | |
| 1.22 | $CH_2CH_2$ | H | 4-$OCF_2CF_3$ | |
| 1.23 | $CH_2CH_2$ | H | 2-$OC_6H_5$ | |
| 1.24 | $CH_2CH_2$ | H | 3-$OC_6H_5$ | |
| 1.25 | $CH_2CH_2$ | H | 4-$OC_6H_5$ | |
| 1.26 | $CH_2CH_2$ | H | 2-$NHC_6H_5$ | |
| 1.27 | $CH_2CH_2$ | H | 3-$NHC_6H_5$ | |
| 1.28 | $CH_2CH_2$ | H | 4-$NHC_6H_5$ | |
| 1.29 | $CH_2CH_2$ | H | 2-$NCH_3C_6H_5$ | |
| 1.30 | $CH_2CH_2$ | H | 3-$NCH_3C_6H_5$ | |
| 1.31 | $CH_2CH_2$ | H | 4-$NCH_3C_6H_5$ | |
| 1.32 | $CH_2CH_2$ | H | 2-$C(O)C_6H_5$ | |
| 1.33 | $CH_2CH_2$ | H | 3-$C(O)C_6H_5$ | |
| 1.34 | $CH_2CH_2$ | H | 4-$C(O)C_6H_5$ | |
| 1.35 | $CH_2CH_2$ | H | 2-$C(NOCH_3)C_6H_5$ | |

TABLE 1-continued

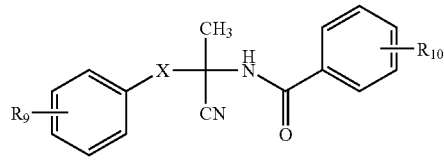

| No. | X | $R_9$ | $R_{10}$ | Phys. data |
|---|---|---|---|---|
| 1.36 | $CH_2CH_2$ | H | 3-$C(NOCH_3)C_6H_5$ | |
| 1.37 | $CH_2CH_2$ | H | 4-$C(NOCH_3)C_6H_5$ | |
| 1.38 | $CH_2CH_2$ | H | 2-$CH(CN)C_6H_5$ | |
| 1.39 | $CH_2CH_2$ | H | 3-$CH(CN)C_6H_5$ | |
| 1.40 | $CH_2CH_2$ | H | 4-$CH(CN)C_6H_5$ | |
| 1.41 | $CH_2CH_2$ | 2-F | H | |
| 1.42 | $CH_2CH_2$ | 2-F | 2-F | |
| 1.43 | $CH_2CH_2$ | 2-F | 3-F | |
| 1.44 | $CH_2CH_2$ | 2-F | 4-F | |
| 1.45 | $CH_2CH_2$ | 2-F | 2-Cl | |
| 1.46 | $CH_2CH_2$ | 2-F | 3-Cl | |
| 1.47 | $CH_2CH_2$ | 2-F | 4-Cl | |
| 1.48 | $CH_2CH_2$ | 2-F | 2-$CH_3$ | |
| 1.49 | $CH_2CH_2$ | 2-F | 3-$CH_3$ | |
| 1.50 | $CH_2CH_2$ | 2-F | 4-$CH_3$ | |
| 1.51 | $CH_2CH_2$ | 2-F | 2-$CF_3$ | |
| 1.52 | $CH_2CH_2$ | 2-F | 3-$CF_3$ | |
| 1.53 | $CH_2CH_2$ | 2-F | 4-$CF_3$ | |
| 1.54 | $CH_2CH_2$ | 2-F | 2-$OCF_3$ | |
| 1.55 | $CH_2CH_2$ | 2-F | 3-$OCF_3$ | |
| 1.56 | $CH_2CH_2$ | 2-F | 4-$OCF_3$ | |
| 1.57 | $CH_2CH_2$ | 2-F | 2-$OCF_2CF_2H$ | |
| 1.58 | $CH_2CH_2$ | 2-F | 3-$OCF_2CF_2H$ | |
| 1.59 | $CH_2CH_2$ | 2-F | 4-$OCF_2CF_2H$ | |
| 1.60 | $CH_2CH_2$ | 2-F | 2-$OCF_2CF_3$ | |
| 1.61 | $CH_2CH_2$ | 2-F | 3-$OCF_2CF_3$ | |
| 1.62 | $CH_2CH_2$ | 2-F | 4-$OCF_2CF_3$ | |
| 1.63 | $CH_2CH_2$ | 2-F | 2-$OC_6H_5$ | |
| 1.64 | $CH_2CH_2$ | 2-F | 3-$OC_6H_5$ | |
| 1.65 | $CH_2CH_2$ | 2-F | 4-$OC_6H_5$ | |
| 1.66 | $CH_2CH_2$ | 2-F | 2-$NHC_6H_5$ | |
| 1.67 | $CH_2CH_2$ | 2-F | 3-$NHC_6H_5$ | |
| 1.68 | $CH_2CH_2$ | 2-F | 4-$NHC_6H_5$ | |
| 1.69 | $CH_2CH_2$ | 2-F | 2-$NCH_3C_6H_5$ | |
| 1.70 | $CH_2CH_2$ | 2-F | 3-$NCH_3C_6H_5$ | |
| 1.71 | $CH_2CH_2$ | 2-F | 4-$NCH_3C_6H_5$ | |
| 1.72 | $CH_2CH_2$ | 2-F | 2-$C(O)C_6H_5$ | |
| 1.73 | $CH_2CH_2$ | 2-F | 3-$C(O)C_6H_5$ | |
| 1.74 | $CH_2CH_2$ | 2-F | 4-$C(O)C_6H_5$ | |
| 1.75 | $CH_2CH_2$ | 2-F | 2-$C(NOCH_3)C_6H_5$ | |
| 1.76 | $CH_2CH_2$ | 2-F | 3-$C(NOCH_3)C_6H_5$ | |
| 1.77 | $CH_2CH_2$ | 2-F | 4-$C(NOCH_3)C_6H_5$ | |
| 1.78 | $CH_2CH_2$ | 2-F | 2-$CH(CN)C_6H_5$ | |
| 1.79 | $CH_2CH_2$ | 2-F | 3-$CH(CN)C_6H_5$ | |
| 1.80 | $CH_2CH_2$ | 2-F | 4-$CH(CN)C_6H_5$ | |
| 1.81 | $CH_2CH_2$ | 3-F | H | |
| 1.82 | $CH_2CH_2$ | 3-F | 2-F | |
| 1.83 | $CH_2CH_2$ | 3-F | 3-F | |
| 1.84 | $CH_2CH_2$ | 3-F | 4-F | |
| 1.85 | $CH_2CH_2$ | 3-F | 2-Cl | |
| 1.86 | $CH_2CH_2$ | 3-F | 3-Cl | |
| 1.87 | $CH_2CH_2$ | 3-F | 4-Cl | |
| 1.88 | $CH_2CH_2$ | 3-F | 2-$CH_3$ | |
| 1.89 | $CH_2CH_2$ | 3-F | 3-$CH_3$ | |
| 1.90 | $CH_2CH_2$ | 3-F | 4-$CH_3$ | |
| 1.91 | $CH_2CH_2$ | 3-F | 2-$CF_3$ | |
| 1.92 | $CH_2CH_2$ | 3-F | 3-$CF_3$ | |
| 1.93 | $CH_2CH_2$ | 3-F | 4-$CF_3$ | |
| 1.94 | $CH_2CH_2$ | 3-F | 2-$OCF_3$ | |
| 1.95 | $CH_2CH_2$ | 3-F | 3-$OCF_3$ | |
| 1.96 | $CH_2CH_2$ | 3-F | 4-$OCF_3$ | |
| 1.97 | $CH_2CH_2$ | 3-F | 2-$OCF_2CF_2H$ | |
| 1.98 | $CH_2CH_2$ | 3-F | 3-$OCF_2CF_2H$ | |
| 1.99 | $CH_2CH_2$ | 3-F | 4-$OCF_2CF_2H$ | |
| 1.100 | $CH_2CH_2$ | 3-F | 2-$OCF_2CF_3$ | |
| 1.101 | $CH_2CH_2$ | 3-F | 3-$OCF_2CF_3$ | |
| 1.102 | $CH_2CH_2$ | 3-F | 4-$OCF_2CF_3$ | |
| 1.103 | $CH_2CH_2$ | 3-F | 2-$OC_6H_5$ | |

TABLE 1-continued

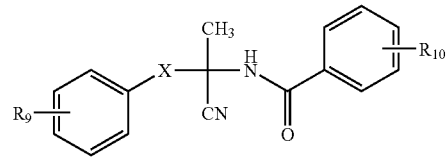

| No. | X | R$_9$ | R$_{10}$ | Phys. data |
|---|---|---|---|---|
| 1.104 | CH$_2$CH$_2$ | 3-F | 3-OC$_6$H$_5$ | |
| 1.105 | CH$_2$CH$_2$ | 3-F | 4-OC$_6$H$_5$ | |
| 1.106 | CH$_2$CH$_2$ | 3-F | 2-NHC$_6$H$_5$ | |
| 1.107 | CH$_2$CH$_2$ | 3-F | 3-NHC$_6$H$_5$ | |
| 1.108 | CH$_2$CH$_2$ | 3-F | 4-NHC$_6$H$_5$ | |
| 1.109 | CH$_2$CH$_2$ | 3-F | 2-NCH$_3$C$_6$H$_5$ | |
| 1.110 | CH$_2$CH$_2$ | 3-F | 3-NCH$_3$C$_6$H$_5$ | |
| 1.111 | CH$_2$CH$_2$ | 3-F | 4-NCH$_3$C$_6$H$_5$ | |
| 1.112 | CH$_2$CH$_2$ | 3-F | 2-C(O)C$_6$H$_5$ | |
| 1.113 | CH$_2$CH$_2$ | 3-F | 3-C(O)C$_6$H$_5$ | |
| 1.114 | CH$_2$CH$_2$ | 3-F | 4-C(O)C$_6$H$_5$ | |
| 1.115 | CH$_2$CH$_2$ | 3-F | 2-C(NOCH$_3$)C$_6$H$_5$ | |
| 1.116 | CH$_2$CH$_2$ | 3-F | 3-C(NOCH$_3$)C$_6$H$_5$ | |
| 1.117 | CH$_2$CH$_2$ | 3-F | 4-C(NOCH$_3$)C$_6$H$_5$ | |
| 1.118 | CH$_2$CH$_2$ | 3-F | 2-CH(CN)C$_6$H$_5$ | |
| 1.119 | CH$_2$CH$_2$ | 3-F | 3-CH(CN)C$_6$H$_5$ | |
| 1.120 | CH$_2$CH$_2$ | 3-F | 4-CH(CN)C$_6$H$_5$ | |
| 1.121 | CH$_2$CH$_2$ | 4-F | H | |
| 1.122 | CH$_2$CH$_2$ | 4-F | 2-F | |
| 1.123 | CH$_2$CH$_2$ | 4-F | 3-F | |
| 1.124 | CH$_2$CH$_2$ | 4-F | 4-F | |
| 1.125 | CH$_2$CH$_2$ | 4-F | 2-Cl | |
| 1.126 | CH$_2$CH$_2$ | 4-F | 3-Cl | |
| 1.127 | CH$_2$CH$_2$ | 4-F | 4-Cl | |
| 1.128 | CH$_2$CH$_2$ | 4-F | 2-CH$_3$ | |
| 1.129 | CH$_2$CH$_2$ | 4-F | 3-CH$_3$ | |
| 1.130 | CH$_2$CH$_2$ | 4-F | 4-CH$_3$ | |
| 1.131 | CH$_2$CH$_2$ | 4-F | 2-CF$_3$ | |
| 1.132 | CH$_2$CH$_2$ | 4-F | 3-CF$_3$ | |
| 1.133 | CH$_2$CH$_2$ | 4-F | 4-CF$_3$ | |
| 1.134 | CH$_2$CH$_2$ | 4-F | 2-OCF$_3$ | |
| 1.135 | CH$_2$CH$_2$ | 4-F | 3-OCF$_3$ | |
| 1.136 | CH$_2$CH$_2$ | 4-F | 4-OCF$_3$ | |
| 1.137 | CH$_2$CH$_2$ | 4-F | 2-OCF$_2$CF$_2$H | |
| 1.138 | CH$_2$CH$_2$ | 4-F | 3-OCF$_2$CF$_2$H | |
| 1.139 | CH$_2$CH$_2$ | 4-F | 4-OCF$_2$CF$_2$H | |
| 1.140 | CH$_2$CH$_2$ | 4-F | 2-OCF$_2$CF$_3$ | |
| 1.141 | CH$_2$CH$_2$ | 4-F | 3-OCF$_2$CF$_3$ | |
| 1.142 | CH$_2$CH$_2$ | 4-F | 4-OCF$_2$CF$_3$ | |
| 1.143 | CH$_2$CH$_2$ | 4-F | 2-OC$_6$H$_5$ | |
| 1.144 | CH$_2$CH$_2$ | 4-F | 3-OC$_6$H$_5$ | |
| 1.145 | CH$_2$CH$_2$ | 4-F | 4-OC$_6$H$_5$ | |
| 1.146 | CH$_2$CH$_2$ | 4-F | 2-NHC$_6$H$_5$ | |
| 1.147 | CH$_2$CH$_2$ | 4-F | 3-NHC$_6$H$_5$ | |
| 1.148 | CH$_2$CH$_2$ | 4-F | 4-NHC$_6$H$_5$ | |
| 1.149 | CH$_2$CH$_2$ | 4-F | 2-NCH$_3$C$_6$H$_5$ | |
| 1.150 | CH$_2$CH$_2$ | 4-F | 3-NCH$_3$C$_6$H$_5$ | |
| 1.151 | CH$_2$CH$_2$ | 4-F | 4-NCH$_3$C$_6$H$_5$ | |
| 1.152 | CH$_2$CH$_2$ | 4-F | 2-C(O)C$_6$H$_5$ | |
| 1.153 | CH$_2$CH$_2$ | 4-F | 3-C(O)C$_6$H$_5$ | |
| 1.154 | CH$_2$CH$_2$ | 4-F | 4-C(O)C$_6$H$_5$ | |
| 1.155 | CH$_2$CH$_2$ | 4-F | 2-C(NOCH$_3$)C$_6$H$_5$ | |
| 1.156 | CH$_2$CH$_2$ | 4-F | 3-C(NOCH$_3$)C$_6$H$_5$ | |
| 1.157 | CH$_2$CH$_2$ | 4-F | 4-C(NOCH$_3$)C$_6$H$_5$ | |
| 1.158 | CH$_2$CH$_2$ | 4-F | 2-CH(CN)C$_6$H$_5$ | |
| 1.159 | CH$_2$CH$_2$ | 4-F | 3-CH(CN)C$_6$H$_5$ | |
| 1.160 | CH$_2$CH$_2$ | 4-F | 4-CH(CN)C$_6$H$_5$ | |
| 1.161 | CH$_2$CH$_2$ | 2-CF$_3$ | H | |
| 1.162 | CH$_2$CH$_2$ | 2-CF$_3$ | 2-F | |
| 1.163 | CH$_2$CH$_2$ | 2-CF$_3$ | 3-F | |
| 1.164 | CH$_2$CH$_2$ | 2-CF$_3$ | 4-F | |
| 1.165 | CH$_2$CH$_2$ | 2-CF$_3$ | 2-Cl | |
| 1.166 | CH$_2$CH$_2$ | 2-CF$_3$ | 3-Cl | |
| 1.167 | CH$_2$CH$_2$ | 2-CF$_3$ | 4-Cl | |
| 1.168 | CH$_2$CH$_2$ | 2-CF$_3$ | 2-CH$_3$ | |
| 1.169 | CH$_2$CH$_2$ | 2-CF$_3$ | 3-CH$_3$ | |
| 1.170 | CH$_2$CH$_2$ | 2-CF$_3$ | 4-CH$_3$ | |
| 1.171 | CH$_2$CH$_2$ | 2-CF$_3$ | 2-CF$_3$ | |

TABLE 1-continued

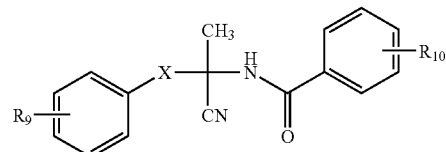

| No. | X | $R_9$ | $R_{10}$ | Phys. data |
|---|---|---|---|---|
| 1.172 | $CH_2CH_2$ | 2-$CF_3$ | 3-$CF_3$ | |
| 1.173 | $CH_2CH_2$ | 2-$CF_3$ | 4-$CF_3$ | |
| 1.174 | $CH_2CH_2$ | 2-$CF_3$ | 2-$OCF_3$ | |
| 1.175 | $CH_2CH_2$ | 2-$CF_3$ | 3-$OCF_3$ | |
| 1.176 | $CH_2CH_2$ | 2-$CF_3$ | 4-$OCF_3$ | M.p. 87–9° |
| 1.177 | $CH_2CH_2$ | 2-$CF_3$ | 2-$OCF_2CF_2H$ | |
| 1.178 | $CH_2CH_2$ | 2-$CF_3$ | 3-$OCF_2CF_2H$ | |
| 1.179 | $CH_2CH_2$ | 2-$CF_3$ | 4-$OCF_2CF_2H$ | viscous oil |
| 1.180 | $CH_2CH_2$ | 2-$CF_3$ | 2-$OCF_2CF_3$ | |
| 1.181 | $CH_2CH_2$ | 2-$CF_3$ | 3-$OCF_2CF_3$ | |
| 1.182 | $CH_2CH_2$ | 2-$CF_3$ | 4-$OCF_2CF_3$ | |
| 1.183 | $CH_2CH_2$ | 2-$CF_3$ | 2-$OC_6H_5$ | |
| 1.184 | $CH_2CH_2$ | 2-$CF_3$ | 3-$OC_6H_5$ | |
| 1.185 | $CH_2CH_2$ | 2-$CF_3$ | 4-$OC_6H_5$ | |
| 1.186 | $CH_2CH_2$ | 2-$CF_3$ | 2-$NHC_6H_5$ | |
| 1.187 | $CH_2CH_2$ | 2-$CF_3$ | 3-$NHC_6H_5$ | |
| 1.188 | $CH_2CH_2$ | 2-$CF_3$ | 4-$NHC_6H_5$ | |
| 1.189 | $CH_2CH_2$ | 2-$CF_3$ | 2-$NCH_3C_6H_5$ | |
| 1.190 | $CH_2CH_2$ | 2-$CF_3$ | 3-$NCH_3C_6H_5$ | |
| 1.191 | $CH_2CH_2$ | 2-$CF_3$ | 4-$NCH_3C_6H_5$ | |
| 1.192 | $CH_2CH_2$ | 2-$CF_3$ | 2-$C(O)C_6H_5$ | |
| 1.193 | $CH_2CH_2$ | 2-$CF_3$ | 3-$C(O)C_6H_5$ | |
| 1.194 | $CH_2CH_2$ | 2-$CF_3$ | 4-$C(O)C_6H_5$ | M.p. 99–101° |
| 1.195 | $CH_2CH_2$ | 2-$CF_3$ | 2-$C(NOCH_3)C_6H_5$ | |
| 1.196 | $CH_2CH_2$ | 2-$CF_3$ | 3-$C(NOCH_3)C_6H_5$ | |
| 1.197 | $CH_2CH_2$ | 2-$CF_3$ | 4-$C(NOCH_3)C_6H_5$ | |
| 1.198 | $CH_2CH_2$ | 2-$CF_3$ | 2-$CH(CN)C_6H_5$ | |
| 1.199 | $CH_2CH_2$ | 2-$CF_3$ | 3-$CH(CN)C_6H_5$ | |
| 1.200 | $CH_2CH_2$ | 2-$CF_3$ | 4-$CH(CN)C_6H_5$ | |
| 1.201 | $CH_2CH_2$ | 3-$CF_3$ | H | |
| 1.202 | $CH_2CH_2$ | 3-$CF_3$ | 2-F | |
| 1.203 | $CH_2CH_2$ | 3-$CF_3$ | 3-F | |
| 1.204 | $CH_2CH_2$ | 3-$CF_3$ | 4-F | |
| 1.205 | $CH_2CH_2$ | 3-$CF_3$ | 2-Cl | |
| 1.206 | $CH_2CH_2$ | 3-$CF_3$ | 3-Cl | |
| 1.207 | $CH_2CH_2$ | 3-$CF_3$ | 4-Cl | |
| 1.208 | $CH_2CH_2$ | 3-$CF_3$ | 2-$CH_3$ | |
| 1.209 | $CH_2CH_2$ | 3-$CF_3$ | 3-$CH_3$ | |
| 1.210 | $CH_2CH_2$ | 3-$CF_3$ | 4-$CH_3$ | |
| 1.211 | $CH_2CH_2$ | 3-$CF_3$ | 2-$CF_3$ | |
| 1.212 | $CH_2CH_2$ | 3-$CF_3$ | 3-$CF_3$ | |
| 1.213 | $CH_2CH_2$ | 3-$CF_3$ | 4-$CF_3$ | |
| 1.214 | $CH_2CH_2$ | 3-$CF_3$ | 2-$OCF_3$ | |
| 1.215 | $CH_2CH_2$ | 3-$CF_3$ | 3-$OCF_3$ | |
| 1.216 | $CH_2CH_2$ | 3-$CF_3$ | 4-$OCF_3$ | |
| 1.217 | $CH_2CH_2$ | 3-$CF_3$ | 2-$OCF_2CF_2H$ | |
| 1.218 | $CH_2CH_2$ | 3-$CF_3$ | 3-$OCF_2CF_2H$ | |
| 1.219 | $CH_2CH_2$ | 3-$CF_3$ | 4-$OCF_2CF_2H$ | |
| 1.220 | $CH_2CH_2$ | 3-$CF_3$ | 2-$OCF_2CF_3$ | |
| 1.221 | $CH_2CH_2$ | 3-$CF_3$ | 3-$OCF_2CF_3$ | |
| 1.222 | $CH_2CH_2$ | 3-$CF_3$ | 4-$OCF_2CF_3$ | |
| 1.223 | $CH_2CH_2$ | 3-$CF_3$ | 2-$OC_6H_5$ | |
| 1.224 | $CH_2CH_2$ | 3-$CF_3$ | 3-$OC_6H_5$ | |
| 1.225 | $CH_2CH_2$ | 3-$CF_3$ | 4-$OC_6H_5$ | |
| 1.226 | $CH_2CH_2$ | 3-$CF_3$ | 2-$NHC_6H_5$ | |
| 1.227 | $CH_2CH_2$ | 3-$CF_3$ | 3-$NHC_6H_5$ | |
| 1.228 | $CH_2CH_2$ | 3-$CF_3$ | 4-$NHC_6H_5$ | |
| 1.229 | $CH_2CH_2$ | 3-$CF_3$ | 2-$NCH_3C_6H_5$ | |
| 1.230 | $CH_2CH_2$ | 3-$CF_3$ | 3-$NCH_3C_6H_5$ | |
| 1.231 | $CH_2CH_2$ | 3-$CF_3$ | 4-$NCH_3C_6H_5$ | |
| 1.232 | $CH_2CH_2$ | 3-$CF_3$ | 2-$C(O)C_6H_5$ | |
| 1.233 | $CH_2CH_2$ | 3-$CF_3$ | 3-$C(O)C_6H_5$ | |
| 1.234 | $CH_2CH_2$ | 3-$CF_3$ | 4-$C(O)C_6H_5$ | |
| 1.235 | $CH_2CH_2$ | 3-$CF_3$ | 2-$C(NOCH_3)C_6H_5$ | |
| 1.236 | $CH_2CH_2$ | 3-$CF_3$ | 3-$C(NOCH_3)C_6H_5$ | |
| 1.237 | $CH_2CH_2$ | 3-$CF_3$ | 4-$C(NOCH_3)C_6H_5$ | |
| 1.238 | $CH_2CH_2$ | 3-$CF_3$ | 2-$CH(CN)C_6H_5$ | |
| 1.239 | $CH_2CH_2$ | 3-$CF_3$ | 3-$CH(CN)C_6H_5$ | |

TABLE 1-continued

| No. | X | R$_9$ | R$_{10}$ | Phys. data |
|---|---|---|---|---|
| 1.240 | CH$_2$CH$_2$ | 3-CF$_3$ | 4-CH(CN)C$_6$H$_5$ | |
| 1.241 | CH$_2$CH$_2$ | 4-CF$_3$ | H | |
| 1.242 | CH$_2$CH$_2$ | 4-CF$_3$ | 2-F | |
| 1.243 | CH$_2$CH$_2$ | 4-CF$_3$ | 3-F | |
| 1.244 | CH$_2$CH$_2$ | 4-CF$_3$ | 4-F | |
| 1.245 | CH$_2$CH$_2$ | 4-CF$_3$ | 2-Cl | |
| 1.246 | CH$_2$CH$_2$ | 4-CF$_3$ | 3-Cl | |
| 1.247 | CH$_2$CH$_2$ | 4-CF$_3$ | 4-Cl | |
| 1.248 | CH$_2$CH$_2$ | 4-CF$_3$ | 2-CH$_3$ | |
| 1.249 | CH$_2$CH$_2$ | 4-CF$_3$ | 3-CH$_3$ | |
| 1.250 | CH$_2$CH$_2$ | 4-CF$_3$ | 4-CH$_3$ | |
| 1.251 | CH$_2$CH$_2$ | 4-CF$_3$ | 2-CF$_3$ | |
| 1.252 | CH$_2$CH$_2$ | 4-CF$_3$ | 3-CF$_3$ | |
| 1.253 | CH$_2$CH$_2$ | 4-CF$_3$ | 4-CF$_3$ | |
| 1.254 | CH$_2$CH$_2$ | 4-CF$_3$ | 2-OCF$_3$ | |
| 1.255 | CH$_2$CH$_2$ | 4-CF$_3$ | 3-OCF$_3$ | |
| 1.256 | CH$_2$CH$_2$ | 4-CF$_3$ | 4-OCF$_3$ | |
| 1.257 | CH$_2$CH$_2$ | 4-CF$_3$ | 2-OCF$_2$CF$_2$H | |
| 1.258 | CH$_2$CH$_2$ | 4-CF$_3$ | 3-OCF$_2$CF$_2$H | |
| 1.259 | CH$_2$CH$_2$ | 4-CF$_3$ | 4-OCF$_2$CF$_2$H | |
| 1.260 | CH$_2$CH$_2$ | 4-CF$_3$ | 2-OCF$_2$CF$_3$ | |
| 1.261 | CH$_2$CH$_2$ | 4-CF$_3$ | 3-OCF$_2$CF$_3$ | |
| 1.262 | CH$_2$CH$_2$ | 4-CF$_3$ | 4-OCF$_2$CF$_3$ | |
| 1.263 | CH$_2$CH$_2$ | 4-CF$_3$ | 2-OC$_6$H$_5$ | |
| 1.264 | CH$_2$CH$_2$ | 4-CF$_3$ | 3-OC$_6$H$_5$ | |
| 1.265 | CH$_2$CH$_2$ | 4-CF$_3$ | 4-OC$_6$H$_5$ | |
| 1.266 | CH$_2$CH$_2$ | 4-CF$_3$ | 2-NHC$_6$H$_5$ | |
| 1.267 | CH$_2$CH$_2$ | 4-CF$_3$ | 3-NHC$_6$H$_5$ | |
| 1.268 | CH$_2$CH$_2$ | 4-CF$_3$ | 4-NHC$_6$H$_5$ | |
| 1.269 | CH$_2$CH$_2$ | 4-CF$_3$ | 2-NCH$_3$C$_6$H$_5$ | |
| 1.270 | CH$_2$CH$_2$ | 4-CF$_3$ | 3-NCH$_3$C$_6$H$_5$ | |
| 1.271 | CH$_2$CH$_2$ | 4-CF$_3$ | 4-NCH$_3$C$_6$H$_5$ | |
| 1.272 | CH$_2$CH$_2$ | 4-CF$_3$ | 2-C(O)C$_6$H$_5$ | |
| 1.273 | CH$_2$CH$_2$ | 4-CF$_3$ | 3-C(O)C$_6$H$_5$ | |
| 1.274 | CH$_2$CH$_2$ | 4-CF$_3$ | 4-C(O)C$_6$H$_5$ | |
| 1.275 | CH$_2$CH$_2$ | 4-CF$_3$ | 2-C(NOCH$_3$)C$_6$H$_5$ | |
| 1.276 | CH$_2$CH$_2$ | 4-CF$_3$ | 3-C(NOCH$_3$)C$_6$H$_5$ | |
| 1.277 | CH$_2$CH$_2$ | 4-CF$_3$ | 4-C(NOCH$_3$)C$_6$H$_5$ | |
| 1.278 | CH$_2$CH$_2$ | 4-CF$_3$ | 2-CH(CN)C$_6$H$_5$ | |
| 1.279 | CH$_2$CH$_2$ | 4-CF$_3$ | 3-CH(CN)C$_6$H$_5$ | |
| 1.280 | CH$_2$CH$_2$ | 4-CF$_3$ | 4-CH(CN)C$_6$H$_5$ | |
| 1.281 | CH$_2$CH$_2$ | 4-OCH$_3$ | 4-OCF$_3$ | M.p. 125° |
| 1.282 | CH$_2$CH$_2$ | 2-CF$_3$, 4,5-F$_2$ | H | |
| 1.283 | CH$_2$CH$_2$ | 2-CF$_3$, 4,5-F$_2$ | 2-F | |
| 1.284 | CH$_2$CH$_2$ | 2-CF$_3$, 4,5-F$_2$ | 3-F | |
| 1.285 | CH$_2$CH$_2$ | 2-CF$_3$, 4,5-F$_2$ | 4-F | |
| 1.286 | CH$_2$CH$_2$ | 2-CF$_3$, 4,5-F$_2$ | 2-Cl | |
| 1.287 | CH$_2$CH$_2$ | 2-CF$_3$, 4,5-F$_2$ | 3-Cl | |
| 1.288 | CH$_2$CH$_2$ | 2-CF$_3$, 4,5-F$_2$ | 4-Cl | |
| 1.289 | CH$_2$CH$_2$ | 2-CF$_3$, 4,5-F$_2$ | 2-CH$_3$ | |
| 1.290 | CH$_2$CH$_2$ | 2-CF$_3$, 4,5-F$_2$ | 3-CH$_3$ | |
| 1.291 | CH$_2$CH$_2$ | 2-CF$_3$, 4,5-F$_2$ | 4-CH$_3$ | |
| 1.292 | CH$_2$CH$_2$ | 2-CF$_3$, 4,5-F$_2$ | 2-CF$_3$ | |
| 1.293 | CH$_2$CH$_2$ | 2-CF$_3$, 4,5-F$_2$ | 3-CF$_3$ | |
| 1.294 | CH$_2$CH$_2$ | 2-CF$_3$, 4,5-F$_2$ | 4-CF$_3$ | |
| 1.295 | CH$_2$CH$_2$ | 2-CF$_3$, 4,5-F$_2$ | 2-OCF$_3$ | |
| 1.296 | CH$_2$CH$_2$ | 2-CF$_3$, 4,5-F$_2$ | 3-OCF$_3$ | |
| 1.297 | CH$_2$CH$_2$ | 2-CF$_3$, 4,5-F$_2$ | 4-OCF$_3$ | |
| 1.298 | CH$_2$CH$_2$ | 2-CF$_3$, 4,5-F$_2$ | 2-OCF$_2$CF$_2$H | |
| 1.299 | CH$_2$CH$_2$ | 2-CF$_3$, 4,5-F$_2$ | 3-OCF$_2$CF$_2$H | |
| 1.300 | CH$_2$CH$_2$ | 2-CF$_3$, 4,5-F$_2$ | 4-OCF$_2$CF$_2$H | |
| 1.301 | CH$_2$CH$_2$ | 2-CF$_3$, 4,5-F$_2$ | 2-OCF$_2$CF$_3$ | |
| 1.302 | CH$_2$CH$_2$ | 2-CF$_3$, 4,5-F$_2$ | 3-OCF$_2$CF$_3$ | |
| 1.303 | CH$_2$CH$_2$ | 2-CF$_3$, 4,5-F$_2$ | 4-OCF$_2$CF$_3$ | |
| 1.304 | CH$_2$CH$_2$ | 2-CF$_3$, 4,5-F$_2$ | 2-OC$_6$H$_5$ | |
| 1.305 | CH$_2$CH$_2$ | 2-CF$_3$, 4,5-F$_2$ | 3-OC$_6$H$_5$ | |
| 1.306 | CH$_2$CH$_2$ | 2-CF$_3$, 4,5-F$_2$ | 4-OC$_6$H$_5$ | |
| 1.307 | CH$_2$CH$_2$ | 2-CF$_3$, 4,5-F$_2$ | 2-NHC$_6$H$_5$ | |

TABLE 1-continued

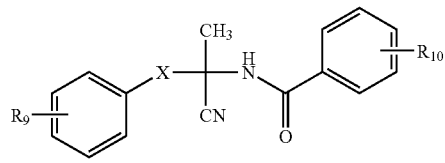

| No. | X | $R_9$ | $R_{10}$ | Phys. data |
|---|---|---|---|---|
| 1.308 | $CH_2CH_2$ | 2-$CF_3$, 4,5-$F_2$ | 3-$NHC_6H_5$ | |
| 1.309 | $CH_2CH_2$ | 2-$CF_3$, 4,5-$F_2$ | 4-$NHC_6H_5$ | |
| 1.310 | $CH_2CH_2$ | 2-$CF_3$, 4,5-$F_2$ | 2-$NCH_3C_6H_5$ | |
| 1.311 | $CH_2CH_2$ | 2-$CF_3$, 4,5-$F_2$ | 3-$NCH_3C_6H_5$ | |
| 1.312 | $CH_2CH_2$ | 2-$CF_3$, 4,5-$F_2$ | 4-$NCH_3C_6H_5$ | |
| 1.313 | $CH_2CH_2$ | 2-$CF_3$, 4,5-$F_2$ | 2-$C(O)C_6H_5$ | |
| 1.314 | $CH_2CH_2$ | 2-$CF_3$, 4,5-$F_2$ | 3-$C(O)C_6H_5$ | |
| 1.315 | $CH_2CH_2$ | 2-$CF_3$, 4,5-$F_2$ | 4-$C(O)C_6H_5$ | |
| 1.316 | $CH_2CH_2$ | 2-$CF_3$, 4,5-$F_2$ | 2-$O(NOCH_3)C_6H_5$ | |
| 1.317 | $CH_2CH_2$ | 2-$CF_3$, 4,5-$F_2$ | 3-$C(NOCH_3)C_6H_5$ | |
| 1.318 | $CH_2CH_2$ | 2-$CF_3$, 4,5-$F_2$ | 4-$O(NOCH_3)C_6H_5$ | |
| 1.319 | $CH_2CH_2$ | 2-$CF_3$, 4,5-$F_2$ | 2-$CH(CN)C_6H_5$ | |
| 1.320 | $CH_2CH_2$ | 2-$CF_3$, 4,5-$F_2$ | 3-$CH(CN)C_6H_5$ | |
| 1.321 | $CH_2CH_2$ | 2-$CF_3$, 4,5-$F_2$ | 4-$CH(CN)C_6H_5$ | |
| 1.322 | $CH_2CH_2$ | 2-O-cyclopropyl, 4,5-$F_2$ | H | |
| 1.323 | $CH_2CH_2$ | 2-O-cyclopropyl, 4,5-$F_2$ | 2-F | |
| 1.324 | $CH_2CH_2$ | 2-O-cyclopropyl, 4,5-$F_2$ | 3-F | |
| 1.325 | $CH_2CH_2$ | 2-O-cyclopropyl, 4,5-$F_2$ | 4-F | |
| 1.326 | $CH_2CH_2$ | 2-O-cyclopropyl, 4,5-$F_2$ | 2-Cl | |
| 1.327 | $CH_2CH_2$ | 2-O-cyclopropyl, 4,5-$F_2$ | 3-Cl | |
| 1.328 | $CH_2CH_2$ | 2-O-cyclopropyl, 4,5-$F_2$ | 4-Cl | |
| 1.329 | $CH_2CH_2$ | 2-O-cyclopropyl, 4,5-$F_2$ | 2-$CH_3$ | |
| 1.330 | $CH_2CH_2$ | 2-O-cyclopropyl, 4,5-$F_2$ | 3-$CH_3$ | |
| 1.331 | $CH_2CH_2$ | 2-O-cyclopropyl, 4,5-$F_2$ | 4-$CH_3$ | |
| 1.332 | $CH_2CH_2$ | 2-O-cyclopropyl, 4,5-$F_2$ | 2-$CF_3$ | |
| 1.333 | $CH_2CH_2$ | 2-O-cyclopropyl, 4,5-$F_2$ | 3-$CF_3$ | |
| 1.334 | $CH_2CH_2$ | 2-O-cyclopropyl, 4,5-$F_2$ | 4-$CF_3$ | |
| 1.335 | $CH_2CH_2$ | 2-O-cyclopropyl, 4,5-$F_2$ | 2-$OCF_3$ | |
| 1.336 | $CH_2CH_2$ | 2-O-cyclopropyl, 4,5-$F_2$ | 3-$OCF_3$ | |
| 1.337 | $CH_2CH_2$ | 2-O-cyclopropyl, 4,5-$F_2$ | 4-$OCF_3$ | |
| 1.338 | $CH_2CH_2$ | 2-O-cyclopropyl, 4,5-$F_2$ | 2-$OCF_2CF_2H$ | |
| 1.339 | $CH_2CH_2$ | 2-O-cyclopropyl, 4,5-$F_2$ | 3-$OCF_2CF_2H$ | |
| 1.340 | $CH_2CH_2$ | 2-O-cyclopropyl, 4,5-$F_2$ | 4-$OCF_2CF_2H$ | |
| 1.341 | $CH_2CH_2$ | 2-O-cyclopropyl, 4,5-$F_2$ | 2-$OCF_2CF_3$ | |
| 1.342 | $CH_2CH_2$ | 2-O-cyclopropyl, 4,5-$F_2$ | 3-$OCF_2CF_3$ | |
| 1.343 | $CH_2CH_2$ | 2-O-cyclopropyl, 4,5-$F_2$ | 4-$OCF_2CF_3$ | |
| 1.344 | $CH_2CH_2$ | 2-O-cyclopropyl, 4,5-$F_2$ | 2-$OC_6H_5$ | |
| 1.345 | $CH_2CH_2$ | 2-O-cyclopropyl, 4,5-$F_2$ | 3-$OC_6H_5$ | |
| 1.346 | $CH_2CH_2$ | 2-O-cyclopropyl; 4,5-$F_2$ | 4-$OC_6H_5$ | |
| 1.347 | $CH_2CH_2$ | 2-O-cyclopropyl, 4,5-$F_2$ | 2-$NHC_6H_5$ | |
| 1.348 | $CH_2CH_2$ | 2-O-cyclopropyl, 4,5-$F_2$ | 3-$NHC_6H_5$ | |
| 1.349 | $CH_2CH_2$ | 2-O-cyclopropyl, 4,5-$F_2$ | 4-$NHC_6H_5$ | |
| 1.350 | $CH_2CH_2$ | 2-O-cyclopropyl, 4,5-$F_2$ | 2-$NCH_3C_6H_5$ | |
| 1.351 | $CH_2CH_2$ | 2-O-cyclopropyl, 4,5-$F_2$ | 3-$NCH_3C_6H_5$ | |
| 1.352 | $CH_2CH_2$ | 2-O-cyclopropyl, 4,5-$F_2$ | 4-$NCH_3C_6H_5$ | |
| 1.353 | $CH_2CH_2$ | 2-O-cyclopropyl, 4,5-$F_2$ | 2-$C(O)C_6H_5$ | |
| 1.354 | $CH_2CH_2$ | 2-O-cyclopropyl, 4,5-$F_2$ | 3-$C(O)C_6H_5$ | |
| 1.355 | $CH_2CH_2$ | 2-O-cyclopropyl, 4,5-$F_2$ | 4-$C(O)C_6H_5$ | |
| 1.356 | $CH_2CH_2$ | 2-O-cyclopropyl, 4,5-$F_2$ | 2-$C(NOCH_3)C_6H_5$ | |
| 1.357 | $CH_2CH_2$ | 2-O-cyclopropyl, 4,5-$F_2$ | 3-$C(NOCH_3)C_6H_5$ | |
| 1.358 | $CH_2CH_2$ | 2-O-cyclopropyl, 4,5-$F_2$ | 4-$C(NOCH_3)C_6H_5$ | |
| 1.359 | $CH_2CH_2$ | 2-O-cyclopropyl, 4,5-$F_2$ | 2-$CH(CN)C_6H_5$ | |
| 1.360 | $CH_2CH_2$ | 2-O-cyclopropyl, 4,5-$F_2$ | 3-$CH(CN)C_6H_5$ | |
| 1.361 | $CH_2CH_2$ | 2-O-cyclopropyl, 4,5-$F_2$ | 4-$CH(CN)C_6H_5$ | |
| 1.362 | $CH_2CH_2$ | 2-$N(CH_3)$-cyclopropyl, 4,5-$F_2$ | H | |
| 1.363 | $CH_2CH_2$ | 2-$N(CH_3)$-cyclopropyl, 4,5-$F_2$ | 2-F | |
| 1.364 | $CH_2CH_2$ | 2-$N(CH_3)$-cyclopropyl, 4,5-$F_2$ | 3-F | |
| 1.365 | $CH_2CH_2$ | 2-$N(CH_3)$-cyclopropyl, 4,5-$F_2$ | 4-F | |
| 1.366 | $CH_2CH_2$ | 2-$N(CH_3)$-cyclopropyl, 4,5-$F_2$ | 2-Cl | |
| 1.367 | $CH_2CH_2$ | 2-$N(CH_3)$-cyclopropyl, 4,5-$F_2$ | 3-Cl | |
| 1.368 | $CH_2CH_2$ | 2-$N(CH_3)$-cyclopropyl, 4,5-$F_2$ | 4-Cl | |
| 1.369 | $CH_2CH_2$ | 2-$N(CH_3)$-cyclopropyl, 4,5-$F_2$ | 2-$CH_3$ | |
| 1.370 | $CH_2CH_2$ | 2-$N(CH_3)$-cyclopropyl, 4,5-$F_2$ | 3-$CH_3$ | |
| 1.371 | $CH_2CH_2$ | 2-$N(CH_3)$-cyclopropyl, 4,5-$F_2$ | 4-$CH_3$ | |
| 1.372 | $CH_2CH_2$ | 2-$N(CH_3)$-cyclopropyl, 4,5-$F_2$ | 2-$CF_3$ | |
| 1.373 | $CH_2CH_2$ | 2-$N(CH_3)$-cyclopropyl, 4,5-$F_2$ | 3-$CF_3$ | |
| 1.374 | $CH_2CH_2$ | 2-$N(CH_3)$-cyclopropyl, 4,5-$F_2$ | 4-$CF_3$ | |
| 1.375 | $CH_2CH_2$ | 2-$N(CH_3)$-cyclopropyl, 4,5-$F_2$ | 2-$OCF_3$ | |

TABLE 1-continued

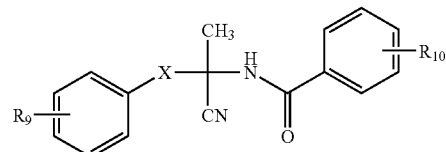

| No. | X | $R_9$ | $R_{10}$ | Phys. data |
|---|---|---|---|---|
| 1.376 | $CH_2CH_2$ | 2-N($CH_3$)-cyclopropyl, 4,5-$F_2$ | 3-$OCF_3$ | |
| 1.377 | $CH_2CH_2$ | 2-N($CH_3$)-cyclopropyl, 4,5-$F_2$ | 4-$OCF_3$ | |
| 1.378 | $CH_2CH_2$ | 2-N($CH_3$)-cyclopropyl, 4,5-$F_2$ | 2-$OCF_2CF_2H$ | |
| 1.379 | $CH_2CH_2$ | 2-N($CH_3$)-cyclopropyl, 4,5-$F_2$ | 3-$OCF_2CF_2H$ | |
| 1.380 | $CH_2CH_2$ | 2-N($CH_3$)-cyclopropyl, 4,5-$F_2$ | 4-$OCF_2CF_2H$ | |
| 1.381 | $CH_2CH_2$ | 2-N($CH_3$)-cyclopropyl, 4,5-$F_2$ | 2-$OCF_2CF_3$ | |
| 1.382 | $CH_2CH_2$ | 2-N($CH_3$)-cyclopropyl, 4,5-$F_2$ | 3-$OCF_2CF_3$ | |
| 1.383 | $CH_2CH_2$ | 2-N($CH_3$)-cyclopropyl, 4,5-$F_2$ | 4-$OCF_2CF_3$ | |
| 1.384 | $CH_2CH_2$ | 2-N($CH_3$)-cyclopropyl, 4,5-$F_2$ | 2-$OC_6H_5$ | |
| 1.385 | $CH_2CH_2$ | 2-N($CH_3$)-cyclopropyl, 4,5-$F_2$ | 3-$OC_6H_5$ | |
| 1.386 | $CH_2CH_2$ | 2-N($CH_3$)-cyclopropyl, 4,5-$F_2$ | 4-$OC_6H_5$ | |
| 1.387 | $CH_2CH_2$ | 2-N($CH_3$)-cyclopropyl, 4,5-$F_2$ | 2-$NHC_6H_5$ | |
| 1.388 | $CH_2CH_2$ | 2-N($CH_3$)-cyclopropyl, 4,5-$F_2$ | 3-$NHC_6H_5$ | |
| 1.389 | $CH_2CH_2$ | 2-N($CH_3$)-cyclopropyl, 4,5-$F_2$ | 4-$NHC_6H_5$ | |
| 1.390 | $CH_2CH_2$ | 2-N($CH_3$)-cyclopropyl, 4,5-$F_2$ | 2-$NCH_3C_6H_5$ | |
| 1.391 | $CH_2CH_2$ | 2-N($CH_3$)-cyclopropyl, 4,5-$F_2$ | 3-$NCH_3C_6H_5$ | |
| 1.392 | $CH_2CH_2$ | 2-N($CH_3$)-cyclopropyl, 4,5-$F_2$ | 4-$NCH_3C_6H_5$ | |
| 1.393 | $CH_2CH_2$ | 2-N($CH_3$)-cyclopropyl, 4,5-$F_2$ | 2-C(O)$C_6H_5$ | |
| 1.394 | $CH_2CH_2$ | 2-N($CH_3$)-cyclopropyl, 4,5-$F_2$ | 3-C(O)$C_6H_5$ | |
| 1.395 | $CH_2CH_2$ | 2-N($CH_3$)-cyclopropyl, 4,5-$F_2$ | 4-C(O)$C_6H_5$ | |
| 1.396 | $CH_2CH_2$ | 2-N($CH_3$)-cyclopropyl, 4,5-$F_2$ | 2-C(N$OCH_3$)$C_6H_5$ | |
| 1.397 | $CH_2CH_2$ | 2-N($CH_3$)-cyclopropyl, 4,5-$F_2$ | 3-C(N$OCH_3$)$C_6H_5$ | |
| 1.398 | $CH_2CH_2$ | 2-N($CH_3$)-cyclopropyl, 4,5-$F_2$ | 4-C(N$OCH_3$)$C_6H_5$ | |
| 1.399 | $CH_2CH_2$ | 2-N($CH_3$)-cyclopropyl, 4,5-$F_2$ | 2-CH(CN)$C_6H_5$ | |
| 1.400 | $CH_2CH_2$ | 2-N($CH_3$)-cyclopropyl, 4,5-$F_2$ | 3-CH(CN)$C_6H_5$ | |
| 1.401 | $CH_2CH_2$ | 2-N($CH_3$)-cyclopropyl, 4,5-$F_2$ | 4-CH(CN)$C_6H_5$ | |
| 1.402 | $CH_2CH_2$ | 2-Br, 4,5-$F_2$ | H | |
| 1.403 | $CH_2CH_2$ | 2-Br, 4,5-$F_2$ | 2-F | |
| 1.404 | $CH_2CH_2$ | 2-Br, 4,5-$F_2$ | 3-F | |
| 1.405 | $CH_2CH_2$ | 2-Br, 4,5-$F_2$ | 4-F | |
| 1.406 | $CH_2CH_2$ | 2-Br, 4,5-$F_2$ | 2-Cl | |
| 1.407 | $CH_2CH_2$ | 2-Br, 4,5-$F_2$ | 3-Cl | |
| 1.408 | $CH_2CH_2$ | 2-Br, 4,5-$F_2$ | 4-Cl | |
| 1.409 | $CH_2CH_2$ | 2-Br, 4,5-$F_2$ | 2-$CH_3$ | |
| 1.410 | $CH_2CH_2$ | 2-Br, 4,5-Fz | 3-$CH_3$ | |
| 1.411 | $CH_2CH_2$ | 2-Br, 4,5-$F_2$ | 4-$CH_3$ | |
| 1.412 | $CH_2CH_2$ | 2-Br, 4,5-$F_2$ | 2-$CF_3$ | |
| 1.413 | $CH_2CH_2$ | 2-Br, 4,5-$F_2$ | 3-$CF_3$ | |
| 1.414 | $CH_2CH_2$ | 2-Br, 4,5-$F_2$ | 4-$CF_3$ | |
| 1.415 | $CH_2CH_2$ | 2-Br, 4,5-$F_2$ | 2-$OCF_3$ | |
| 1.416 | $CH_2CH_2$ | 2-Br, 4,5-$F_2$ | 3-$OCF_3$ | |
| 1.417 | $CH_2CH_2$ | 2-Br, 4,5-$F_2$ | 4-$OCF_3$ | |
| 1.418 | $CH_2CH_2$ | 2-Br, 4,5-$F_2$ | 2-$OCF_2CF_2H$ | |
| 1.419 | $CH_2CH_2$ | 2-Br, 4,5-$F_2$ | 3-$OCF_2CF_2H$ | |
| 1.420 | $CH_2CH_2$ | 2-Br, 4,5-$F_2$ | 4-$OCF_2CF_2H$ | |
| 1.421 | $CH_2CH_2$ | 2-Br, 4,5-$F_2$ | 2-$OCF_2CF_3$ | |
| 1.422 | $CH_2CH_2$ | 2-Br, 4,5-$F_2$ | 3-$OCF_2CF_3$ | |
| 1.423 | $CH_2CH_2$ | 2-Br, 4,5-$F_2$ | 4-$OCF_2CF_3$ | |
| 1.424 | $CH_2CH_2$ | 2-Br, 4,5-$F_2$ | 2-$OC_6H_5$ | |
| 1.425 | $CH_2CH_2$ | 2-Br, 4,5-$F_2$ | 3-$OC_6H_5$ | |
| 1.426 | $CH_2CH_2$ | 2-Br, 4,5-$F_2$ | 4-$OC_6H_5$ | |
| 1.427 | $CH_2CH_2$ | 2-Br, 4,5-$F_2$ | 2-$NHC_6H_5$ | |
| 1.428 | $CH_2CH_2$ | 2-Br, 4,5-$F_2$ | 3-$NHC_6H_5$ | |
| 1.429 | $CH_2CH_2$ | 2-Br, 4,5-$F_2$ | 4-$NHC_6H_5$ | |
| 1.430 | $CH_2CH_2$ | 2-Br, 4,5-$F_2$ | 2-$NCH_3C_6H_5$ | |
| 1.431 | $CH_2CH_2$ | 2-Br, 4,5-$F_2$ | 3-$NCH_3C_6H_5$ | |
| 1.432 | $CH_2CH_2$ | 2-Br, 4,5-$F_2$ | 4-$NCH_3C_6H_5$ | |
| 1.433 | $CH_2CH_2$ | 2-Br, 4,5-$F_2$ | 2-C(O)$C_6H_5$ | |
| 1.434 | $CH_2CH_2$ | 2-Br, 4,5-$F_2$ | 3-C(O)$C_6H_5$ | |
| 1.435 | $CH_2CH_2$ | 2-Br, 4,5-$F_2$ | 4-C(O)$C_6H_5$ | |
| 1.436 | $CH_2CH_2$ | 2-Br, 4,5-$F_2$ | 2-C(N$OCH_3$)$C_6H_5$ | |
| 1.437 | $CH_2CH_2$ | 2-Br, 4,5-$F_2$ | 3-C(N$OCH_3$)$C_6H_5$ | |
| 1.438 | $CH_2CH_2$ | 2-Br, 4,5-$F_2$ | 4-C(N$OCH_3$)$C_6H_5$ | |
| 1.439 | $CH_2CH_2$ | 2-Br, 4,5-$F_2$ | 2-CH(CN)$C_6H_5$ | |
| 1.440 | $CH_2CH_2$ | 2-Br, 4,5-$F_2$ | 3-CH(CN)$C_6H_5$ | |
| 1.441 | $CH_2CH_2$ | 2-Br, 4,5-$F_2$ | 4-CH(CN)$C_6H_5$ | |

BIOLOGICAL EXAMPLES

1. In vivo test against *Trichostrongylus colubriformis* and *Haemonchus contortus* in Mongolian gerbils (*Medrones unguiculatus*) by peroral administration Six- to eight-week-old Mongolian gerbils are infected, using manufactured feed, with in each case approximately 2 000 larvae of the 3rd stage of *T. colubriformis* and *H. contortus*. Six days after infecting, the gerbils are lightly anaesthetized with $N_2O$ and are treated by peroral administration with the test compounds, dissolved in a mixture of 2 parts of DMSO and 1 part of polyethylene glycol (PEG 300), with amounts of 100, 32 and 10–0.1 mg/kg. On day 9 (3 days after treating), when most of the *H. contortus* larvae still existing are in the late 4th stage and most of the *T. colubriformis* are immature adults, the gerbils are sacrificed in order to count the worms. The activity is calculated in % reduction in the number of worms in each gerbil by comparison with the geometric mean of the number of worms from 8 infected and untreated gerbils.

In this test, a large decrease in the nematode infestation is obtained with compounds of the formula I, in particular from Table 1.

The following test methods can be employed in investigating the insecticidal and/or acaricidal action of the compounds of the formula I on animals and plants.

2. Action Against $L_1$ Larvae of *Lucilia sericata*

1 ml of an aqueous suspension of the active substance to be tested is thus mixed at approximately 50° C. with 3 ml of a special medium for raising larvae, so that a homogenate with an active ingredient content of either 250 or 125 ppm is formed. Approximately 30 *Lucilia larvae* ($L_1$) are introduced into each test tube sample. After 4 days, the mortality rate is determined.

3. Acaricidal Action Against *Boophilus microplus* (Biarra strain)

An adhesive tape is attached horizontally to a PVC plate such that 10 female *Boophilus microplus* ticks (Biarra strain) which have sucked themselves full of blood can be adhesively attached to the tape via their backs in a row, next to one another. Each tick is injected, using an injection needle, with 1 µl of a liquid which is a 1:1 mixture of polyethylene glycol and acetone and in which a certain amount of active ingredient of alternatively 1, 0.1 or 0.01 µg per tick is dissolved. Control animals receive an injection not comprising an active ingredient. After the treatment, the animals are kept in an insectarium under standard conditions at approximately 28° C. and 80% relative humidity until egg laying has occurred and the larvae have hatched from the eggs of the control animals. The activity of a test substance is determined using the $IR_{90}$, i.e. that dose of active ingredient is ascertained at which, after 30 days, 9 out of 10 female ticks (=90%) lay eggs which are not able to hatch.

4. In vitro Activity Against Fed *Boophilus microplus* Females (Biarra):

4×10 fed female ticks of the OP-resistant Biarra strain are attached to an adhesive tape and are covered for 1 h with a wad of cotton which has been impregnated with an emulsion or suspension of the test compound in concentrations in each case of 500, 125, 31 and 8 ppm. The mortality, egg laying and larval hatching are evaluated 28 days later.

An indication of the activity of the test compounds is the number of the females which
quickly die, before laying eggs,
survive for some time, without laying eggs,
lay eggs in which no embryos develop,
lay eggs in which embryos develop but from which no larvae hatch, and
lay eggs in which embryos develop and from which larvae hatch normally in 26 to 27 days.

5. In vitro Activity Against Nymphs of *Amblyomma hebraeum*

About 5 hungry nymphs are placed in a polystyrene test tube comprising 2 ml of the test compound in solution, suspension or emulsion.

After immersing for 10 minutes and shaking for 2×10 seconds on a vortex mixer, the test tubes are plugged with a thick wad of cotton wool and are inverted. As soon as all the liquid has been soaked up by the wad of cotton, the wad is pushed halfway into the still inverted test tube, so that most of the liquid is squeezed out of the wad of cotton and flows into a petri dish placed underneath.

The test tubes are now, until evaluation, stored at ambient temperature in a room lit by daylight. After 14 days, the test tubes are immersed in a beaker of boiling water. If, in reaction to the heat, the ticks begin to move, the test substance is inactive at the test concentration; otherwise, the ticks are considered to be dead and the test substance is considered to be active at the test concentration. All substances are tested in a concentration range from 0.1 to 100 ppm.

6. Action Against *Dermanyssus gallinae*

2 to 3 ml of a solution comprising 10 ppm of active ingredient and approximately 200 mites (*Dermanyssus gallinae*) at various development stages are placed in a glass vessel open at the top. The vessel is subsequently plugged with a wad of cotton, shaken for 10 minutes, until the mites have been completely wetted, and then briefly inverted, so that the remaining test solution can be absorbed by the cotton wool. After 3 days, the mortality of the mites is ascertained by counting the dead individuals and is given in percent.

7. Action Against *Musca domestica*

A sugar cube is treated with a solution of the test substance such that the concentration of test substance in the sugar, after drying overnight, is 250 ppm. This treated cube is placed with a wet wad of cotton and 10 adult *Musca domestica* of an OP-resistant strain on an aluminium dish, is covered with a beaker and is incubated at 25° C. The mortality rate is determined after 24 hours.

What is claimed is:

1. A compound of formula I $$\text{Ar}_1 \underset{\underset{O}{\|}}{\overset{\overset{R_1 \ R_2}{\diagdown \ /}}{\underset{|}{C}}} \underset{CN}{\overset{}{\underset{|}{C}}} - X - \text{Ar}_2, \quad I$$

in which
$Ar_1$ and $Ar_2$ are, independently of one another, unsubstituted or mono- or polysubstituted phenyl, in which the substituents can be independent of one another and are chosen from the group consisting of halogen, nitro, cyano, $C_1$–$C_6$alkyl, halo-$C_1$–$C_6$alkyl, $C_1$–$C_6$alkoxy, halo-$C_1$–$C_6$alkoxy, $C_2$–$C_6$alkenyl, halo-$C_2$–$C_6$alkenyl, $C_2$–$C_6$alkynyl, $C_3$–$C_6$cycloalkyl, $C_3$–$C_6$cycloalkyloxy, $C_3$–$C_6$cycloalkylamino, $C_3$–$C_6$cycloalkylthio, $C_2$–$C_6$alkenyloxy, halo-$C_2$–$C_6$alkenyloxy, $C_1$–$C_6$alkylthio, halo-$C_1$–$C_6$alkylthio, $C_1$–$C_6$alkylsulfonyloxy, halo-$C_1$–$C_6$alkylsulfonyloxy, $C_1$–$C_6$alkylsulfinyl, halo-$C_1$–$C_6$alkylsulfinyl, $C_1$–$C_6$alkylsulfonyl, halo-$C_1$–$C_6$alkylsulfonyl, $C_2$–$C_6$alkenylthio, halo-$C_2$–$C_6$alkenylthio, $C_2$–$C_6$alkenylsulfinyl, halo-$C_2$–$C_6$alkenylsulfinyl, $C_2$–$C_6$alkenylsulfonyl, halo-$C_2$–$C_6$alkenylsulfonyl, $C_1$–$C_6$alkylamino, di-$C_1$–$C_6$alkylamino, $C_1$–$C_6$alkylsulfonylamino, halo-$C_1$–$C_6$alkylsulfonylamino, $C_1$–$C_6$alkylcarbonyl, halo-$C_1$–$C_6$alkylcarbonyl, $C_1$–$C_6$alkoxycarbonyl, $C_1$–$C_6$alkylaminocarbonyl and di-$C_1$–$C_6$alkylaminocarbonyl; unsubstituted or mono- or polysubstituted phenylamino; unsubstituted or mono- or polysubstituted phenylcarbonyl; unsubstituted or mono- or polysubstituted phenylmethoxymino; unsubstituted or mono- or polysubstituted phenylhydroxymethyl; unsubstituted or mono- or polysubstituted 1-phenyl-1-hydroxyethyl; unsubstituted or mono- or polysubstituted phenylchloromethyl; unsubstituted or mono- or polysubstituted phenylcyanomethyl; unsubstituted or mono- or polysubstituted phenyl, in which the substituents in each case can be independent of one another and are chosen from the group consisting of halogen, nitro, cyano, $C_1$–$C_6$alkyl, halo-$C_1$–$C_6$alkyl, $C_1$–$C_6$alkoxy, halo-$C_1$–$C_6$alkoxy, $C_1$–$C_6$alkylthio, halo-$C_1$–$C_6$alkylthio, $C_1$–$C_6$alkylsulfinyl, halo-$C_1$–$C_6$alkylsulfinyl, $C_1$–$C_6$alkylsulfonyl and halo-$C_1$–$C_6$alkylsulfonyl; unsubstituted or mono- or polysubstituted phenoxy, in which the substituents can be independent of one another and are chosen from the group consisting of halogen, nitro, cyano, $C_1$–$C_6$alkyl, halo-$C_1$–$C_6$alkyl, $C_1$–$C_6$alkoxy, halo-$C_1$–$C_6$alkoxy, $C_1$–$C_6$alkylthio, halo-$C_1$–$C_6$alkylthio, $C_1$–$C_6$alkylsulfinyl, halo-$C_1$–$C_6$alkylsulfinyl, $C_1$–$C_6$alkylsulfonyl and halo-$C_1$–$C_6$alkylsulfonyl; unsubstituted or mono- or polysubstituted phenylacetylenyl, in which the substituents can be independent of one another and are chosen from the group consisting of halogen, nitro, cyano, $C_1$–$C_6$alkyl, halo-$C_1$–$C_6$alkyl, $C_1$–$C_6$alkoxy, halo-$C_1$–$C_6$alkoxy, $C_1$–$C_6$alkylthio, halo-$C_1$–$C_6$alkylthio, $C_1$–$C_6$alkylsulfinyl, $C_1$–$C_6$alkylsulfonyl and halo-$C_1$–$C_6$alkylsulfonyl; and unsubstituted or mono- or polysubstituted pyridyloxy, in which the substituents can be independent of one another and are chosen from the group consisting of halogen, nitro, cyano, $C_1$–$C_6$alkyl, halo-$C_1$–$C_6$alkyl, $C_1$–$C_6$alkoxy, halo-$C_1$–$C_6$alkoxy, $C_1$–$C_6$alkylthio, halo-$C_1$–$C_6$alkylthio, $C_1$–$C_6$alkylsulfinyl, halo-$C_1$–$C_6$alkylsulfinyl, $C_1$–$C_6$alkylsulfonyl and halo-$C_1$–$C_6$alkylsulfonyl;

unsubstituted or mono- or polysubstituted hetaryl, in which the substituents can be independent of one another and are chosen from the group consisting of halogen, nitro, cyano, $C_1$–$C_6$alkyl, halo-$C_1$–$C_6$alkyl, $C_1$–$C_6$alkoxy, halo-$C_1$–$C_6$alkoxy, $C_2$–$C_6$alkenyloxy, halo-$C_2$–$C_6$alkenyloxy, $C_1$–$C_6$alkylthio, halo-$C_1$–$C_6$alkylthio, $C_1$–$C_6$alkylsulfinyl, halo-$C_1$–$C_6$alkylsulfinyl, $C_2$–$C_6$alkenylthio, halo-$C_2$–$C_6$alkenylthio, $C_2$–$C_6$alkenylsulfinyl, halo-$C_2$–$C_6$alkenylsulfinyl, $C_1$–$C_6$alkylsulfonyl, halo-$C_1$–$C_6$alkylsulfonyl, $C_2$–$C_6$alkenylsulfonyl, halo-$C_2$–$C_6$alkenylsulfonyl, $C_1$–$C_6$alkylamino and di-$C_1$–$C_6$alkylamino; or unsubstituted or mono- or polysubstituted naphthyl or quinolyl, in which the substituents can be independent of one another and are chosen from the group consisting of halogen, nitro, cyano, $C_1$–$C_6$alkyl, halo-$C_1$–$C_6$alkyl, $C_1$–$C_6$alkoxy, halo-$C_1$–$C_6$alkoxy, $C_2$–$C_6$alkenyloxy, halo-$C_2$–$C_6$alkenyloxy, $C_1$–$C_6$alkylthio, halo-$C_1$–$C_6$alkylthio, $C_1$–$C_6$alkylsulfinyl, halo-$C_1$–$C_6$alkylsulfinyl, $C_2$–$C_6$alkenylthio, halo-$C_2$–$C_6$alkenylthio, $C_2$–$C_6$alkenylsulfinyl, halo-$C_2$–$C_6$alkenylsulfinyl, $C_1$–$C_6$alkylsulfonyl, halo-$C_1$–$C_6$alkylsulfonyl, $C_2$–$C_6$alkenylsulfonyl, halo-$C_2$–$C_6$alkenylsulfonyl, $C_1$–$C_6$alkylamino and di-$C_1$–$C_6$alkylamino;

$R_1$ is hydrogen, $C_1$–$C_6$alkyl, halo-$C_1$–$C_6$alkyl, allyl or $C_1$–$C_6$alkoxymethyl;

$R_2$, $R_3$, $R_4$, $R_5$, $R_6$, $R_7$ and $R_8$ are either, independently of one another, hydrogen, halogen, unsubstituted or mono- or polyhalogenated $C_1$–$C_6$alkyl, unsubstituted or mono- or polyhalogenated $C_2$–$C_6$alkenyl, unsubstituted or mono- or polyhalogenated $C_2$–$C_6$alkynyl; unsubstituted or mono- or polysubstituted $C_1$–$C_6$alkoxy, unsubstituted or mono- or polysubstituted halo-$C_1$–$C_6$alkoxy, unsubstituted or mono- or polysubstituted $C_3$–$C_6$cycloalkyl, in which the substituents in each case can be independent of one another and are chosen from the group consisting of halogen and $C_1$–$C_6$alkyl; or unsubstituted or mono- or polysubstituted phenyl, in which the substituents can be independent of one another and are chosen from the group consisting of halogen, nitro, cyano, $C_1$–$C_6$alkyl, halo-$C_1$–$C_6$alkyl, $C_1$–$C_6$alkoxy, halo-$C_1$–$C_6$alkoxy, $C_1$–$C_6$alkylthio, halo-$C_1$–$C_6$alkylthio, $C_1$–$C_6$alkylsulfinyl, halo-$C_1$–$C_6$alkylsulfinyl, $C_1$–$C_6$alkylsulfonyl, halo-$C_1$–$C_6$alkylsulfonyl, $C_1$–$C_6$alkylamino or di-$C_1$–$C_6$alkylamino;

or $R_2$ and $R_3$ are jointly $C_2$–$C_6$alkylene; and

X is $C(R_3)(R_4)$—$C(R_5)(R_6)$ or $C(R_7)$=$C(R_8)$.

2. A compound of the formula I according to claim 1, in which $Ar_1$ and $Ar_2$ are, independently of one another, unsubstituted or mono- or polysubstituted phenyl, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_3$–$C_5$cycloalkyl, $C_3$–$C_5$cycloalkyloxy, $C_3$–$C_5$cycloalkylamino, $C_1$–$C_5$alkylthio, halo-$C_1$–$C_5$alkylthio, $C_1$–$C_4$alkylamino, di-$C_1$–$C_4$alkylamino, $C_1$–$C_4$alkylcarbonyl, halo-$C_1$–$C_4$alkylcarbonyl, $C_1$–$C_4$alkoxycarbonyl, $C_1$–$C_4$alkylaminocarbonyl and di-$C_1$–$C_4$alkylaminocarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio; unsubstituted or mono- or polysubstituted phenoxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio; and unsubstituted or mono- or polysubstituted pyridyloxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio.

3. A compound of the formula I according to claim 1, in which $Ar_1$ and $Ar_2$ are, independently of one another, unsubstituted or mono- or polysubstituted phenyl, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_3$–$C_5$cycloalkyl, $C_3$–$C_5$cycloalkyloxy, $C_3$–$C_5$cycloalkylamino, $C_1$–$C_4$alkylcarbonyl, halo-$C_1$–$C_4$alkylcarbonyl and $C_1$–$C_4$alkoxycarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, nitro, cyano, $C_1$–$C_4$alkyl, halo-$C_1$–$C_4$alkyl, $C_1$–$C_4$alkoxy and halo-$C_1$–$C_4$alkoxy; and unsubstituted or mono- or polysubstituted phenoxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy and halo-$C_1$–$C_4$alkoxy.

4. A compound of the formula I according to claim 1, in which $Ar_1$ and $Ar_2$ are, independently of one another, unsubstituted or mono- or polysubstituted phenyl, in which the substituents can be independent of one another and are chosen from the group consisting of halogen, cyano, $C_1$–$C_2$alkyl, halo-$C_1$–$C_2$alkyl, $C_1$–$C_2$alkoxy, halo-$C_1$–$C_2$alkoxy, $C_3$–$C_4$cycloalkyl, $C_3$–$C_4$cycloalkyloxy, $C_3$–$C_4$cycloalkylamino, $C_1$–$C_2$alkylcarbonyl, halo-$C_1$–$C_2$alkylcarbonyl and $C_1$–$C_2$alkoxycarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, cyano, $C_1$–$C_2$alkyl, halo-$C_1$–$C_2$alkyl, $C_1$–$C_2$alkoxy and halo-$C_1$–$C_2$alkoxy; and unsubstituted or mono- or polysubstituted phenoxy, in which the substituents can be independent of one another and are chosen from the group consisting of halogen, cyano, $C_1$–$C_2$alkyl, halo-$C_1$–$C_2$alkyl, $C_1$–$C_2$alkoxy and halo-$C_1$–$C_2$alkoxy.

5. A compound of the formula I according to claim 1, in which $R_1$ is hydrogen, $C_1$–$C_4$alkyl or halo-$C_1$–$C_4$alkyl.

6. A compound of the formula I according to claim 1, in which $R_1$ is hydrogen or $C_1$–$C_2$alkyl.

7. A compound of the formula I according to claim 1, in which $R_1$ is hydrogen.

8. A compound of the formula I according to claim 1, in which $R_2$, $R_3$, $R_4$, $R_5$, $R_6$, $R_7$ and $R_8$ are, independently of one another, hydrogen, halogen, unsubstituted or mono- or polyhalogenated $C_1$–$C_4$alkyl, unsubstituted or mono- or polyhalogenated $C_2$–$C_4$alkenyl, unsubstituted or mono- or polyhalogenated $C_2$–$C_4$alkynyl; unsubstituted or mono- or polysubstituted $C_1$–$C_4$alkoxy, unsubstituted or mono- or polysubstituted halo-$C_1$–$C_4$alkoxy, $C_3$–$C_5$cycloalkyl, or unsubstituted or mono- or polysubstituted phenyl, in which the substituents can be independent of one another and are chosen from the group consisting of halogen, cyano, $C_1$–$C_4$alkyl, halo-$C_1$–$C_4$-alkyl, $C_1$–$C_4$alkoxy and halo-$C_1$–$C_4$alkoxy.

9. A compound of the formula I according to claim 1, in which $R_2$, $R_3$, $R_4$, $R_5$, $R_6$, $R_7$ and $R_8$ are, independently of one another, hydrogen, unsubstituted or mono- or polyhalogenated $C_1$–$C_4$alkyl, $C_3$–$C_5$cycloalkyl, or unsubstituted or mono- or polysubstituted phenyl, in which the substituents can be independent of one another and are chosen from the group consisting of halogen, $C_1$–$C_2$alkyl or halo-$C_1$–$C_4$alkyl.

10. A compound of the formula I according to claim 1, in which $R_2$, $R_3$, $R_4$, $R_5$, $R_6$, $R_7$ and $R_8$ are, independently of one another, hydrogen, $C_1$–$C_2$alkyl or $C_3$–$C_5$cycloalkyl.

11. A compound of the formula I according to claim 1, in which X is $C(R_3)(R_4)$—$C(R_5)(R_6)$.

12. A compound of the formula I according to claim 1, in which $Ar_1$ and $Ar_2$ are, independently of one another, unsubstituted or mono- or polysubstituted phenyl, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_3$–$C_5$cycloalkyl, $C_3$–$C_5$cycloalkyloxy, $C_3$–$C_5$cycloalkylamino, $C_1$–$C_5$alkylthio, halo-$C_1$–$C_5$alkylthio, $C_1$–$C_4$alkylamino, di-$C_1$–$C_4$alkylamino, $C_1$–$C_4$alkylcarbonyl, halo-$C_1$–$C_4$alkylcarbonyl, $C_1$–$C_4$alkoxycarbonyl, $C_1$–$C_4$alkylaminocarbonyl and di-$C_1$–$C_4$alkylaminocarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio; unsubstituted or mono- or polysubstituted phenoxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$-alkylthio; and unsubstituted or mono- or polysubstituted pyridyloxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_1$–$C_4$alkylthio and halo-$C_1$–$C_4$alkylthio;

$R_1$ is hydrogen, $C_1$–$C_4$alkyl or halo-$C_1$–$C_4$alkyl;

$R_2$, $R_3$, $R_4$, $R_5$, $R_6$, $R_7$ and $R_8$ are, independently of one another, hydrogen, halogen, unsubstituted or mono- or polyhalogenated $C_1$–$C_4$alkyl, unsubstituted or mono- or polyhalogenated $C_2$–$C_4$alkenyl, unsubstituted or mono- or polyhalogenated $C_2$–$C_4$alkynyl; unsubstituted or mono- or polysubstituted $C_1$–$C_4$alkoxy, unsubstituted or mono- or polysubstituted halo-$C_1$–$C_4$alkoxy, $C_3$–$C_5$cycloalkyl, or unsubstituted or mono- or polysubstituted phenyl, in which the substituents can be independent of one another and are chosen from the group consisting of halogen, cyano, $C_1$–$C_4$alkyl, halo-$C_1$–$C_4$alkyl, $C_1$–$C_4$alkoxy and halo-$C_1$–$C_4$alkoxy; and X is $C(R_3)(R_4)$—$C(R_5)(R_6)$.

13. A compound of the formula I according to claim 1, in which $Ar_1$ and $Ar_2$ are particularly, independently of one another, unsubstituted or mono- or polysubstituted phenyl, in which the substituents can be independent of one another and are chosen from the group consisting of halogen, nitro, cyano, $C_1$–$C_4$alkyl, halo-$C_1$–$C_4$alkyl, $C_1$–$C_4$alkoxy, halo-$C_1$–$C_4$alkoxy, $C_3$–$C_5$cycloalkyl, $C_3$–$C_5$cycloalkyloxy, $C_3$–$C_5$cycloalkylamino, $C_1$–$C_4$alkylcarbonyl, halo-$C_1$–$C_4$alkylcarbonyl and $C_1$–$C_4$alkoxycarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, nitro, cyano, $C_1$–$C_4$alkyl, halo-$C_1$–$C_4$alkyl, $C_1$–$C_4$alkoxy and halo-$C_1$–$C_4$alkoxy; and unsubstituted or mono- or polysubstituted phenoxy, in which the substituents can be independent of one another and are chosen from the group consisting of halogen, nitro, cyano, $C_1$–$C_4$alkyl, halo-$C_1$–$C_4$alkyl, $C_1$–$C_4$alkoxy and halo-$C_1$–$C_4$alkoxy;

$R_1$ is hydrogen or $C_1$–$C_2$alkyl;

$R_2$, $R_3$, $R_4$, $R_5$, $R_6$, $R_7$ and $R_8$ are, independently of one another, hydrogen, unsubstituted or mono- or polyhalogenated $C_1$–$C_4$alkyl, $C_3$–$C_5$cycloalkyl, or unsubstituted or mono- or polysubstituted phenyl, in which the substituents can be independent of one another and are chosen from the group consisting of halogen, $C_1$–$C_2$alkyl or halo-$C_1$–$C_4$alkyl; and X is $C(R_3)(R_4)$—$C(R_5)(R_6)$.

14. A compound of the formula I according to claim 1, in which $Ar_1$ and $Ar_2$ are, independently of one another, unsubstituted or mono- or polysubstituted phenyl, in which the substituents can be independent of one another and are chosen from the group consisting of halogen, cyano, $C_1$–$C_2$alkyl, halo-$C_1$–$C_2$alkyl, $C_1$–$C_2$alkoxy, halo-$C_1$–$C_2$alkoxy, $C_3$–$C_4$cycloalkyl, $C_3$–$C_4$cycloalkyloxy, $C_3$–$C_4$cycloalkylamino, $C_1$–$C_2$alkylcarbonyl, halo-$C_1$–$C_2$alkylcarbonyl and $C_1$–$C_2$alkoxycarbonyl; unsubstituted or mono- or polysubstituted phenylamino; unsubstituted or mono- or polysubstituted phenylcarbonyl; unsubstituted or mono- or polysubstituted phenyl, in which the substituents in each case can be independent of one another and are chosen from the group consisting of halogen, cyano, $C_1$–$C_2$alkyl, halo-$C_1$–$C_2$alkyl, $C_1$–$C_2$alkoxy and halo-$C_1$–$C_2$alkoxy; and unsubstituted or mono- or polysubstituted phenoxy, in which the substituents can be independent of one another and are chosen from the group consisting of halogen, cyano, $C_1$–$C_2$alkyl, halo-$C_1$–$C_2$alkyl, $C_1$–$C_2$alkoxy and halo-$C_1$–$C_2$alkoxy;

$R_1$ is hydrogen;

$R_2$, $R_3$, $R_4$, $R_5$, $R_6$, $R_7$ and $R_8$ are, independently of one another, hydrogen, $C_1$–$C_2$alkyl or $C_3$–$C_5$cycloalkyl; and X is $C(R_3)(R_4)$—$C(R_5)(R_6)$.

15. A compound of the formula I according to claim 1, with the name N-(1-cyano-1-methyl-3-[2-trifluoromethylphenyl]propyl)-4-trifluoromethoxybenzamide.

16. A method for the preparation of a compound of the formula I, according to claim 1, comprising the reaction of a compound of the formula II

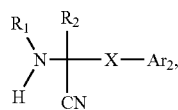
II which is known or can be prepared by analogy to relevant known compounds and in which $R_1$, $R_2$, X and $Ar_2$ are as defined above in the formula I, with a compound of the formula III

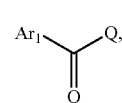
III which is known or can be prepared by analogy to relevant known compounds and in which $Ar_1$ is as defined above in the formula I and Q is a leaving group, if desired in the presence of a basic catalyst, and in each case, if desired, the conversion of a compound of the formula I obtainable according to the process, in each case in the free form or in the salt form, to another compound of the formula I, the separation of a mixture of isomers obtainable according to the process and the isolation of the desired isomer and/or the conversion of a free compound of the formula I obtainable according to the process to a salt or the conversion of a salt of a compound of the formula I obtainable according to the process to the free compound of the formula I or to another salt.

17. A composition for controlling parasites, which comprises, in addition to carriers and/or dispersants, at least one compound of the formula I according to claim 1.

18. A method for controlling parasites comprising applying to said parasites or its habitat a parasiticidal effective amount of at least one compound of formula I of claim 1.

19. The method of claim 18 wherein said parasiticidal effective amount of said at least one compound of formula I of claim 1 is administered to an animal host of said parasite.

20. The method of claim 19 whereby said at least one compound of formula I of claim 1 is administered to said animal host topically, perorally, parenterally, or subcutaneously.

21. The method of claim 18 whereby said compound is in a formulation consisting of the group of pour-on, spot-on, tablet, chewie, powder, boli, capsules, suspension, emulsion, solution, injectable, water-additive, and food-additive.

22. The method of claim 18 wherein said parasites are endo-parasites.

23. The method of claim 22 wherein said endo-parasites are helminthes.

24. A method of treating an animal for parasites comprising administering to said animal in need of treatment thereof a parasiticidal effective amount of the composition of claim 17.

25. The method of claim 24 wherein said administration to said animal is topically, perorally, parenterally, or subcutaneously.

26. The method of claim 24 wherein said composition of claim 17 is in a formulation consisting of the group of pour-on, spot-on, tablet, chewie, powder, boli, capsules, suspension, emulsion, solution, injectable, water-additive, and food-additive.

27. The method of claim 24 wherein said parasites are endo-parasites.

28. The method of claim 27 wherein said endo-parasites are helminthes.

* * * * *